(12) United States Patent
Chiasson

(10) Patent No.: US 9,814,295 B2
(45) Date of Patent: Nov. 14, 2017

(54) CONSUMER PRODUCTS APPLICATOR AND RELATED METHODS

(71) Applicant: Freshceuticals, Inc., Burlington, VT (US)

(72) Inventor: James P. Chiasson, Burlington, VT (US)

(73) Assignee: FRESHCEUTICALS, INC., Burlington, VT (US)

( * ) Notice: Subject to any disclaimer, the term of this patent is extended or adjusted under 35 U.S.C. 154(b) by 106 days.

(21) Appl. No.: 14/836,492

(22) Filed: Aug. 26, 2015

(65) Prior Publication Data

US 2016/0058156 A1   Mar. 3, 2016

Related U.S. Application Data

(60) Provisional application No. 62/042,231, filed on Aug. 26, 2014.

(51) Int. Cl.
| | |
|---|---|
| *A45D 40/24* | (2006.01) |
| *A61M 35/00* | (2006.01) |
| *A45D 34/04* | (2006.01) |
| *A45D 40/26* | (2006.01) |
| *A45D 34/00* | (2006.01) |

(52) U.S. Cl.
CPC .......... *A45D 40/24* (2013.01); *A45D 34/041* (2013.01); *A45D 40/261* (2013.01); *A61M 35/003* (2013.01); *A45D 2034/005* (2013.01); *A45D 2200/055* (2013.01); *A45D 2200/058* (2013.01); *A45D 2200/1009* (2013.01)

(58) Field of Classification Search
CPC .... A45D 34/041; A45D 40/24; A45D 40/261; A61M 35/003
See application file for complete search history.

(56) References Cited

U.S. PATENT DOCUMENTS

| | | | | |
|---|---|---|---|---|
| 5,088,849 | A | * | 2/1992 | Johnson ................. A45D 34/04 401/140 |
| 6,606,938 | B2 | | 8/2003 | Taylor |
| 7,032,818 | B2 | | 4/2006 | Thomas et al. |
| 7,157,816 | B2 | | 1/2007 | Pilcher et al. |
| D549,964 | S | | 9/2007 | Roth et al. |
| 7,320,691 | B2 | | 1/2008 | Pilcher et al. |
| 7,386,906 | B2 | | 6/2008 | Roth et al. |
| 7,445,372 | B1 | * | 11/2008 | Engel .................. B01F 7/00758 222/145.6 |
| D601,803 | S | | 10/2009 | Reishus et al. |
| 7,786,626 | B2 | | 8/2010 | Reishus et al. |
| 7,789,092 | B2 | | 9/2010 | Akridge et al. |
| 8,091,802 | B2 | | 1/2012 | Federov |
| 8,091,803 | B2 | | 1/2012 | Federov |

(Continued)

FOREIGN PATENT DOCUMENTS

WO  PCT/US2015/046977   12/2015

*Primary Examiner* — Jennifer C Chiang
*Assistant Examiner* — Bradley Oliver
(74) *Attorney, Agent, or Firm* — Birch Tree IP Law & Strategy PLLC; Jamie T. Gallagher

(57) ABSTRACT

Consumer product application device and method involving a plurality of reservoirs and intelligence for selectively controlling the delivery of consumer products from each of the plurality of reservoirs in series and/or in combination to an applicator element. The reservoirs may be part of a removable cartridge.

17 Claims, 11 Drawing Sheets

(56) References Cited

U.S. PATENT DOCUMENTS

| | | | |
|---|---|---|---|
| 8,091,804 B2 | 1/2012 | Federov | |
| 8,096,489 B2 | 1/2012 | Federov | |
| 8,361,527 B2 | 1/2013 | Winkler et al. | |
| D679,502 S | 4/2013 | Itano et al. | |
| 8,430,338 B2 | 4/2013 | Duru et al. | |
| D683,139 S | 5/2013 | Chikos et al. | |
| 8,469,909 B2 | 6/2013 | Pilcher et al. | |
| 8,484,788 B2 | 7/2013 | Brewer et al. | |
| 8,516,948 B2 | 8/2013 | Zimmerman et al. | |
| D698,449 S | 1/2014 | Brewer et al. | |
| D698,932 S | 2/2014 | Brewer et al. | |
| 8,641,702 B2 | 2/2014 | Pilcher et al. | |
| 8,740,917 B2 | 6/2014 | Pilcher et al. | |
| 8,746,586 B2 | 6/2014 | Duru et al. | |
| 9,060,595 B2 | 6/2015 | Grez et al. | |
| 2002/0144603 A1 | 10/2002 | Taylor | |
| 2003/0006281 A1 | 1/2003 | Thomas et al. | |
| 2005/0277950 A1 | 12/2005 | Pilcher et al. | |
| 2005/0278876 A1 | 12/2005 | Roth et al. | |
| 2005/0278877 A1 | 12/2005 | Akridge et al. | |
| 2005/0280319 A1 | 12/2005 | Pilcher et al. | |
| 2006/0108247 A1 | 5/2006 | Liechty et al. | |
| 2007/0095362 A1 | 5/2007 | Koopah | |
| 2007/0142845 A1 | 6/2007 | Akridge et al. | |
| 2007/0225645 A1* | 9/2007 | Tarinelli | A61M 37/00 604/131 |
| 2007/0258749 A1 | 11/2007 | Gueret | |
| 2008/0063673 A1 | 3/2008 | Akridge | |
| 2008/0097355 A1 | 4/2008 | Pilcher et al. | |
| 2008/0106156 A1 | 5/2008 | Reishus et al. | |
| 2008/0134902 A1 | 6/2008 | Zimmerman et al. | |
| 2008/0160509 A1 | 7/2008 | Akridge et al. | |
| 2008/0262397 A1 | 10/2008 | Habatjou | |
| 2009/0177125 A1 | 7/2009 | Pilcher et al. | |
| 2009/0200392 A1 | 8/2009 | Duru et al. | |
| 2009/0200398 A1 | 8/2009 | Duru et al. | |
| 2009/0206174 A1 | 8/2009 | Arnaud et al. | |
| 2009/0266915 A1 | 10/2009 | Federov | |
| 2009/0266916 A1 | 10/2009 | Federov | |
| 2009/0272316 A1 | 11/2009 | Arnaud et al. | |
| 2009/0306577 A1 | 12/2009 | Akridge et al. | |
| 2010/0147883 A1 | 6/2010 | Federov | |
| 2010/0170964 A1 | 7/2010 | Federov | |
| 2010/0185322 A1* | 7/2010 | Bylsma | A61M 35/003 700/239 |
| 2010/0300479 A1 | 12/2010 | Reishus et al. | |
| 2010/0300480 A1 | 12/2010 | Pilcher et al. | |
| 2011/0082409 A1 | 4/2011 | Reishus et al. | |
| 2012/0037184 A1 | 2/2012 | Czetty et al. | |
| 2012/0058226 A1 | 3/2012 | Winkler et al. | |
| 2012/0233798 A1 | 9/2012 | Brewer et al. | |
| 2013/0122817 A1 | 5/2013 | Pivaudran | |
| 2014/0135665 A1 | 5/2014 | Pilcher et al. | |
| 2014/0148822 A1 | 5/2014 | Abdulla Ibrahim Al Mahza | |
| 2014/0305458 A1 | 10/2014 | Brewer et al. | |
| 2014/0309662 A1 | 10/2014 | Brewer et al. | |
| 2014/0366288 A1 | 12/2014 | Grez et al. | |
| 2014/0367131 A1 | 12/2014 | Grez et al. | |
| 2014/0373003 A1 | 12/2014 | Grez et al. | |
| 2015/0141884 A1 | 5/2015 | Thiebaut et al. | |
| 2015/0150754 A1 | 6/2015 | Kadra et al. | |
| 2015/0174387 A1 | 6/2015 | McInnes et al. | |
| 2016/0270511 A1* | 9/2016 | Wee | A61M 35/003 |

\* cited by examiner

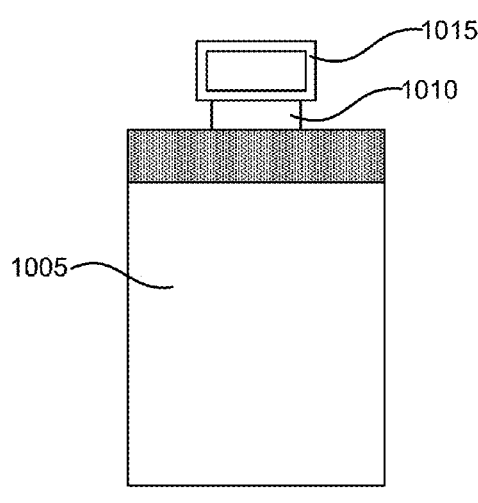
FIG. 10
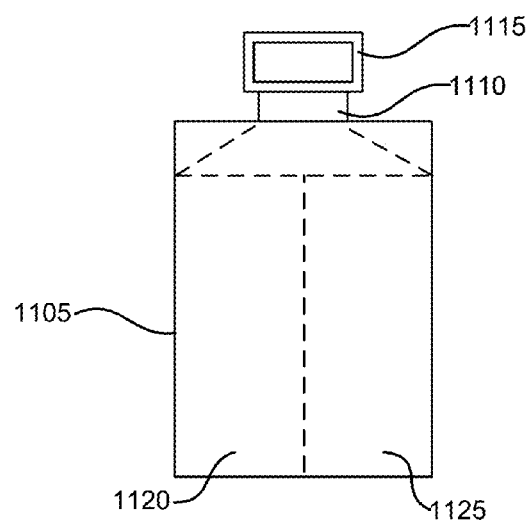
FIG. 11
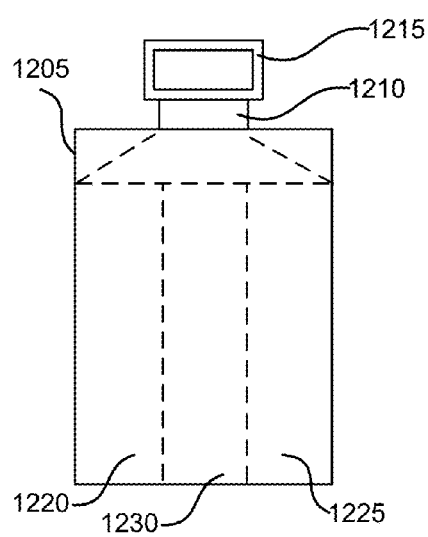
FIG. 12
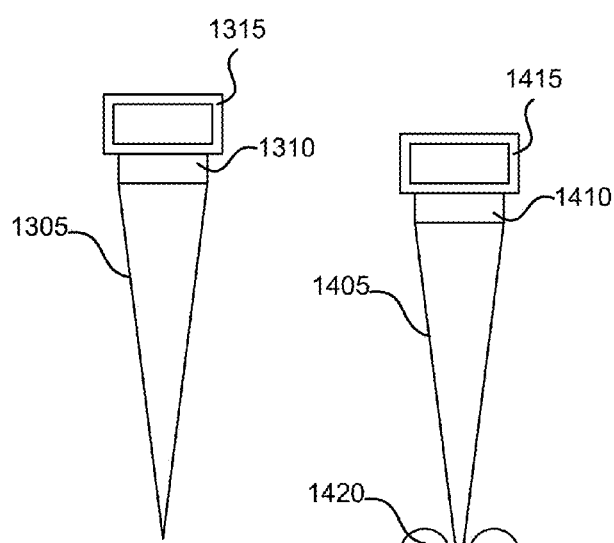
FIG. 13
FIG. 14

CONSUMER PRODUCTS APPLICATOR AND RELATED METHODS

RELATED APPLICATION DATA

This application claims the benefit of priority of U.S. Provisional Patent Application Ser. No. 62/042,231, filed on Aug. 26, 2014, and titled "Consumer Products Applicator and Related Methods," which is incorporated by reference herein in its entirety.

FIELD OF INVENTION

The present invention generally relates to the field of consumer products for application to the surface of a subject. In particular, the present invention is directed to a consumer products applicator and related methods.

BACKGROUND

Devices for applying consumer products to a subject generally involve a user manually placing a consumer product on the surface to be treated or upon the applicator prior to application. The amount of the product to apply, the viability of the product, the amount of time to apply the product, etc. are often inconsistently performed by the user. Several companies have manufactured products that assist a user in application and some provide moving components, such as rotating and sonic brushes. For example, various brush applicators are provided under the CLARISONIC brand by Pacific Bioscience Laboratories, Inc. of Redmond, Wash. However, improved applicator functionality is desired.

SUMMARY OF THE DISCLOSURE

In one implementation, a device for application of consumer products to an outer surface of a subject is provided. The device includes a plurality of reservoirs, each of the plurality of reservoirs for holding a consumer product; an applicator element configured to apply one or more of the consumer products to an outer surface of a subject; a pumping element connected to the plurality of reservoirs, the pumping element configured to deliver one or more of the consumer products to a first surface of the applicator element; and a processing element for controlling the pumping element to selectively deliver a first consumer product from a first one of the plurality of reservoirs to the applicator element in series and/or in combination with a second consumer product from a second one of the plurality of reservoirs.

In another implementation, a device for application of consumer products to an outer surface of a subject is provided. The device includes a plurality of reservoirs, each of the plurality of reservoirs for holding a consumer product, the plurality of reservoirs positioned in a removable cartridge, the removable cartridge including one or more connection elements for connecting the removable cartridge to the device; an applicator element configured to apply one or more of the consumer products to an outer surface of a subject; a pumping element connected to the plurality of reservoirs, the pumping element configured to deliver one or more of the consumer products to a first surface of the applicator element, the pumping element including a piston component positioned in each of the plurality of reservoirs, each piston component actuated by a gas pressure to move the piston in a direction toward a consumer product within the corresponding reservoir of the plurality of reservoirs; and a processing element for controlling the pumping element to selectively deliver a first consumer product from a first one of the plurality of reservoirs to the applicator element in series and/or in combination with a second consumer product from a second one of the plurality of reservoirs.

In yet another implementation, a method of applying a plurality of consumer products to a surface of a subject with an automated application device, the automated application device including an application element and a plurality of reservoirs, each of the plurality of reservoirs configured to contain a consumer product and provide the consumer product to the application element, the plurality of reservoirs positioned in a cartridge, the cartridge removably connectable to the automated application device, is provided. The method includes automatically providing a first pressure on a first consumer product in a first reservoir of the plurality of reservoirs, the first pressure delivering a first portion of the first consumer product to a surface of an applicator element of the automated application device; contacting the applicator element with the first consumer product to the surface of the subject; providing an automatic motion to the applicator element; providing a second pressure on a second consumer product in a second reservoir of the plurality of reservoirs after the contacting the applicator element to the surface of the subject, the second pressure delivering a first portion of the second consumer product to a surface of the applicator element; and contacting the applicator element with the second consumer product to the surface of the subject.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 10 illustrates an exterior view of one exemplary implementation of a removable cartridge having one or more reservoirs for holding one or more consumer products and attachment to an applicator device;

FIG. 11 illustrates a cross sectional view of another exemplary implementation of a removable cartridge for holding one or more consumer products;

FIG. 12 illustrates a cross sectional view of yet another exemplary implementation of a removable cartridge for holding one or more consumer products;

FIG. 13 illustrates a cross sectional side perspective view of one exemplary implementation of a removable cartridge;

FIG. 14 illustrates a cross sectional side perspective view of another exemplary implementation of a removable cartridge;

DETAILED DESCRIPTION

Figure 1:
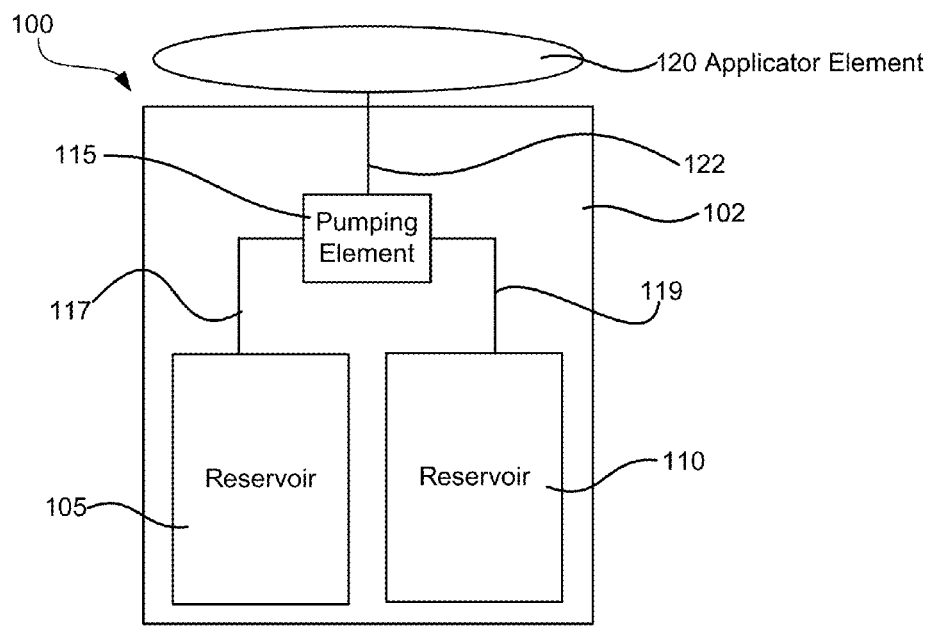
FIG. 1 illustrates a cross sectional view of one implementation of a device for application of one or more consumer products to a surface of a subject.

FIG. 1 illustrates a cross sectional view of one implementation of a device 100 for application of one or more consumer products to a surface (e.g., the skin, the hair, a nail, a cuticle, mucous membrane, a scalp, etc.) of a user. Proper application of consumer products can influence the effect of the product. Example consumer products for application include, but are not limited to, a skin formulation, a hair formulation, a nail formulation (e.g., a toenail formulation, a fingernail formulation), a scalp formulation, a pharmaceutical formulation, a mineral formulation, a biologic formulation, anti-itch formulation, anti-lice formulation, a prescription formulation, a bed sore treatment formulation, a diabetic ulcer treatment formulation, an anti-acne formulation, and any combinations thereof. Example skin formulations include, but are not limited to, a skin cleanser, a skin moisturizer, a facial product, a medicament, anti-itch formulation, anti-head lice formulation, psoriasis formulation, an eczema formulation, a scar removal formulation, a tattoo removal formulation, and any combinations thereof. Example hair formulations include, but are not limited to, a hair cleanser, a hair conditioner, a hair growth medicament, other hair medicaments, a hair coloring, and any combinations thereof. Example scalp formulations include, but are not limited to, a moisturizer, a cleanser, a hair growth medicament, a dandruff medicament, an anti-lice formulation, an anti-tic formulation, an anti-itch formulation, and any combinations thereof. Example pharmaceutical formulations include, but are not limited to, a hair growth formulation, a nasal formulation, an anti-itch formulation, an anti-lice formulation, a psoriasis formulation, an eczema formulation, a scar reduction formulation, and any combinations thereof. Some consumer products have sensitivities to environmental factors, such as light, oxygen, etc. In such examples, the viability of a consumer product over time may be impacted by its exposure to the environment (e.g., after first opening of a container).

Consumer products come in a variety of forms including, but not limited to, products in a fluid form, in a solid form, in a semi-solid form, and any combinations thereof. Example fluid forms include, but are not limited to, a lotion, a cream, a liquid, a suspension, a gel, a vapor (e.g., water vapor), a foam, a gas, a serum, and any combinations thereof. Example solid and/or semi-solid materials include, but are not limited to, a nanoparticle, a microparticle, a beaded particle, a gel bead, a powder, and any combinations thereof. A fluid consumer product may include one or more solid and/or semisolid materials therein. For example, a fluid consumer product may have an abrasive solid and/or semi-solid material added to assist with exfoliation and/or cleansing. Other solid and/or semisolid materials may also be present. In one example, a solid and/or semisolid material is present as a nanoparticle. In another example, as solid and/or semisolid material is present as a beaded particle. In other examples, a consumer products may be primarily in a solid form (e.g. as a powder). Further, a consumer product may include a combination of solid, liquid, or other components. For example, a consumer product may include small spheres of one formulation suspended in a gel and/or a liquid. In another example, one reservoir of an application device may include a composition of one form (e.g., solid, gel, liquid, etc.) and another reservoir may contain a composition of a different form. In one such example, the two compositions may be combined during application to a surface of a subject. In another such example, the two compositions may be dispensed serially one after another during a particular treatment.

A user of a device for application of one or more consumer products according to the current disclosure can be any live subject that requires application of a consumer product to a surface of the subject. Example live subjects include, but are not limited to, a human, an animal (e.g., a pet, a dog, a cat, a horse, etc.), and any combinations thereof. When a non-human live subject is the user, an additional human user may be involved with the manipulation and/or operation of the device.

Device 100 includes a body 102. Body 102 can include any material capable of supporting the included components of the device and be suitable for the use by the user for a particular consumer product and/or application environment. Example materials include, but are not limited to, a plastic, a metal, a rubber, a silicon molded part, a glass, a pressurized aluminum, and any combinations thereof. Body 102 may be designed and configured to be water resistant and/or waterproof. Example ways to increase water resistance and/or waterproofing include, but are not limited to, selection of one or more materials for body 102 that have a high level of water resistance (e.g., are non-porous), sealing (e.g., with a gasket, with a potting material, with a sealant) joints and openings in body 102, use of foam inside the body, and any combinations thereof. Foam (or other material) may also be utilized inside body 102 to provide sound dampening in and around components of device 100. Body 102 may have any shape and physical configuration suitable for the application of one or more consumer products to a surface of a user. Example configuration features for body 102 include, but are not limited to, a portability, a compact structure, a grip structure for handheld use by user, a shape and configuration conformed to a hand of a user, a shape and configuration for providing an extension to the reach of a user (e.g., for application to a user's back), and any combinations thereof.

Device 100 includes one or more reservoirs, each for holding a consumer product or a portion thereof. Device 100 includes a reservoir 105 and a reservoir 110. A device for application of a consumer product according to the present disclosure can have any number of reservoirs. Example factors that may influence the number of reservoirs that may be suitable for a given device include, but are not limited to, a desired application purpose, a desired consumer product(s), an application environment, a desired mixture of consumer products, volatility of one or more consumer products prior to combination, and any combinations thereof. Device 100 and other examples in this disclosure, are shown with two reservoirs for exemplary purposes only. In another example, a device may have a single reservoir and any one or more of the other components, features, and/or aspects of a device for application of a consumer product disclosed herein. In yet another example, a device may have three or more reservoirs for holding one or more consumer products in conjunction with any one or more of the other components, features, and/or aspects of a device for application of a consumer product disclosed herein.

In one exemplary aspect, multiple reservoirs may allow various features and functionalities to device 100 that can improve application of one or more consumer products to a surface of a user. Example features and functionalities include, but are not limited to, combination (e.g., mixing) of two or more consumer products for application, combination (e.g., mixing) of two or more components of a consumer product for application, separation of two or more consumer products prior to application, separation of two or more components of a consumer product prior to application, sequential application of two or more consumer products, sequential application of two or more components of a consumer product, other combinations and sequences of application, and any combinations thereof. In one example, a consumer product may be stored in two or more reservoirs as separated components prior to application. In one such example, two or more components of a consumer product may have a shorter lifespan (e.g., be more volatile to degradation) when combined such that separation prior to use and combination at the time (or about the time) of application can extend the shelf life of the consumer product. In another example, different consumer products can be kept separated prior to use and combined at the time (or about the time) of application and/or applied sequentially for a desired effect. In one example, two or more consumer products can be applied sequentially by an applicator device of the current disclosure using instructions stored in a memory. In another such example, a schedule may be utilized by the applicator device to have applications at specified times during a day, week, or other period (e.g., reminded to a user using the intelligence of an applicator device as discussed herein).

A reservoir (such as reservoir 105, 110) may include an opening (not shown in FIG. 1) in the reservoir and/or body 102 to allow a user to fill the reservoir with a consumer product. In one example, an opening may include a sealable opening (e.g., a door, a hole with a self-closing gasket, etc.). In another implementation, a reservoir may be part of a cartridge or other compartment that is removable from device 100. A removable cartridge may include one or more reservoirs. A reservoir of a cartridge or other compartment could be filled with one or more consumer products while in device 100 and/or while separated from device 100. In one example, a removable cartridge/compartment may be a cartridge that is prefilled with one or more consumer products. In one such example, the cartridge/compartment is provided to a user prefilled (e.g., sold to a consumer prefilled), such as a presealed pod-like cartridge. In another such example, the cartridge/compartment is prefilled by a user of device 100 (e.g., from another container with the desired consumer product). A removable cartridge may be disposable after one or more uses. Examples of removable cartridges/compartments are discussed further below (e.g., with respect to FIGS. 8A, 8B, 9A, and 9B).

Device 100 also includes a pumping element 115 that is connected to reservoir 105 via a connector 117 and to reservoir 110 via connector 119. Pumping element 115 is also connected to an applicator element 120 via a connector 122. Any one or more connectors that allow one or more consumer products to be delivered from a reservoir to an applicator element can be sufficient. Example connectors include, but are not limited to, a conduit, a piping, a tubing, a chamber passageway, a manifold, a valve, a mixing chamber, and any combinations thereof. Selection, number, and configuration of a connector may take into consideration any number of factors. Such factors may include, but are not limited to, a physical characteristic of a consumer product to be delivered (e.g., viscosity), placement/location of pumping element in relation to one or more reservoirs, placement/location of one or more reservoirs in relation to an applicator element, a type of interface between a connector and an applicator element, one or more other factors, and any combinations thereof. One or more manifolds and/or one or more valves in a connector may be controlled by a processing element (e.g., discussed further below). In one such example, a processing element may selectively allow passage of a consumer product from one reservoir and block passage of a consumer product from another reservoir. In another such example, a processing element may selectively allow a force from a pumping element to be applied to a consumer product in one reservoir and block that force from being applied to another consumer product in another reservoir.

A pumping element (such as pumping element 115) is one or more components designed and configured to deliver one or more consumer products from a reservoir to a surface of an applicator element. In one exemplary aspect, a pumping element provides a force that causes a consumer product to move from a reservoir to an applicator element (e.g., via one or more connectors). Example forces include, but are not limited to, a pushing force, a sucking force, a peristaltic pumping force, a mechanical force, a pneumatic force, and any combinations thereof. Example components for a pumping element include, but are not limited to, a micro-fluid pump, a mechanical pump, a peristaltic pump, a piezoelectric element, a gas cartridge (e.g., a carbon dioxide cartridge), a pneumatic pump, a mechanical assist component (e.g., a piston), a mechanical pressure driving component (e.g., a motor for driving a piston), any subcomponents thereof, and any combination thereof. Example mechanical components of a pumping element include, but are not limited to, a piston, a roller mechanism, and any combinations thereof. In one exemplary aspect, a mechanical component of a pumping element may provide pressure directly to one or more reservoirs to force one or more consumer products from the respective reservoir to an applicator element (e.g., via one or more connectors). One example of a mechanical roller mechanism is discussed further below with respect to FIG. 14. Example piston driven pumping elements are discussed further below with respect to FIGS. 16A and 17A. In an alternative embodiment a pumping element, such as pumping element 115/215 may be omitted. In such an embodiment, a user may provide manual pressure to one or more reservoirs to provide force for movement of one or more consumer products from a respective reservoir to an applicator element. One such example is discussed further below with respect to FIG. 13.

Various combinations of pumping element components and configurations are envisioned for a device according to this disclosure (e.g., device 100, 200, and other devices discussed further below). In one example, a pumping element includes a mechanical drive device connected to a piston that is positioned to push a consumer product out of a reservoir to an applicator element (e.g., via one or more connectors). In another example, a pumping element includes a piston that is driven by air pressure (e.g., provided by a pneumatic pump, a gas cartridge, etc.), the piston positioned to push a consumer product out of a reservoir to an applicator element (e.g., via one or more connectors). In still another example, a pumping element includes a peristaltic pump that provides a pressure that causes a consumer product to move from a reservoir to an applicator element (e.g., via one or more connectors). In yet another example, a pumping element includes a piezoelectric element positioned and configured to provide a vibrating force to a consumer product causing the consumer product to change states (e.g., to a gas) and/or to form a mist, the changed consumer product being moved from a reservoir to an applicator element by the piezoelectric element and/or one or more other components of the pumping element. In still yet another example, a pumping element includes a microfluid pump that provides a pressure to move a consumer product from a reservoir to an applicator element. In a further example, a pumping element may have a different configuration that acts upon the connection(s) and/or the one or more reservoirs to facilitate the delivery of the one or more consumer products to an applicator element.

Figure 2:
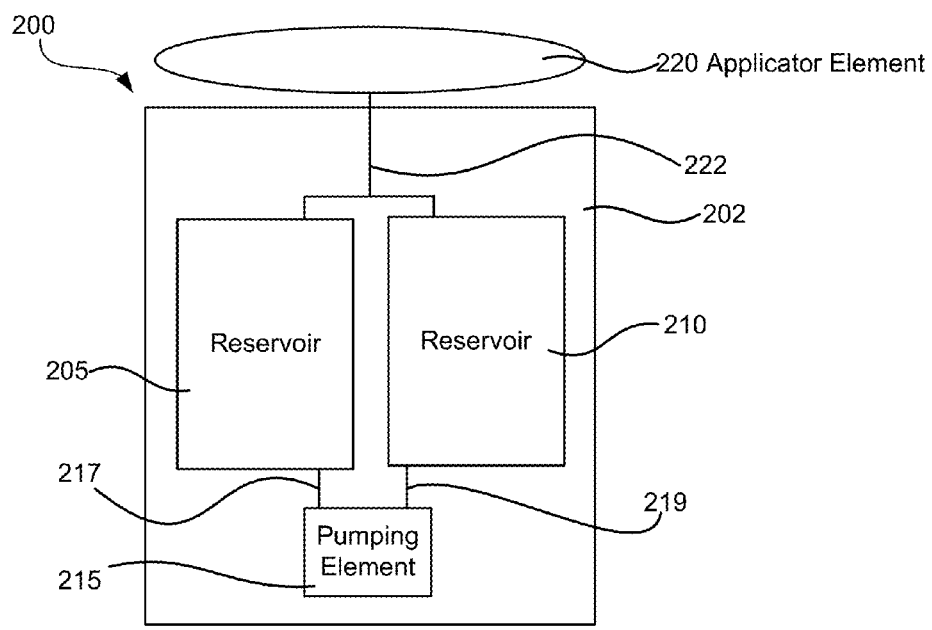
FIG. 2 illustrates another example of a configuration of a device for application of one or more consumer products.

Pumping element 115 is shown in device 100 as being positioned between reservoirs 105, 110 and applicator element 120. In other examples, a pumping element may be positioned such that one or more reservoirs are between the pumping element and an applicator element. One such example is illustrated in FIG. 2. FIG. 2 illustrates an example of a configuration of a device 200 having a reservoir 205 and a reservoir 210 positioned between a pumping element 215 and an applicator element 220. For purposes of efficient disclosure, components of device 200 that are similar to those of device 100 have similar features, aspects, functionalities, options, and alternatives as those discussed above with respect to device 100 (including the ability for optional components that are not shown in FIG. 1, but are discussed therein), except where described in a contrary fashion with respect to device 200. Additional features, aspects, functionalities, options, and alternatives may be discussed with respect to a like component of device 200, and are contemplated to be applicable (where not contrary to the discussion above) to the like components of device 100. Connectors 217 and 219 are positioned between pumping element 215 and reservoirs 205/210. In another example, pumping element 215 may provide pressure via a single output connector (not shown) that splits (e.g., with a valve, y-connector, manifold, etc.) to connect to reservoir 205 and reservoir 210. A connector 222 is provided between reservoirs 205 and 210 and applicator element 220. In one exemplary implementation of device 200, pumping element 215 provides air pressure via connectors 217 and 219 to reservoirs 205 and 210. The air pressure enters one end of reservoirs 205 and 210 causing a force to exert on a piston inside each reservoir (not shown). The piston acts on consumer product on the other side of the piston to force the consumer product out via connector 222 to applicator element 220.

Devices 100 and 200 are shown with various connectors (117, 119, 122, 217, 219, 222) between components. It is envisioned that a device according to this disclosure may have any number of connectors between one or more reservoirs and an applicator element and any number of connectors between a pumping element and one or more reservoirs. Where one connector is shown in examples connecting multiple elements, it is contemplated that multiple connectors may be utilized. For example, connector 222 that connects both reservoir 205 and 210 to applicator element 222 may be substituted with a separate connector between reservoir 205 and applicator element 220 and another connector between reservoir 210 and applicator element 220. Conversely, where a multiple connectors are shown between multiple components, components, a single connector (e.g., one including one or more valves) may be substituted. For example, connectors 217 and 219 could be substituted with a single connector that provides a force from pumping element 215 to reservoir 205 and to reservoir 210 (e.g., simultaneous force, selective force such as with a valve component). It is also contemplated that connectors between a pumping element and a reservoir may be omitted, connectors between a pumping element and a reservoir be part of the pumping element itself, connectors between a pumping element and a reservoir be part of the reservoir itself, connectors between a reservoir and an applicator element be omitted, connectors between a reservoir and an applicator element be part of the reservoir itself, connectors between a reservoir and an applicator element be part of the applicator element itself, and any combinations thereof. For example, a reservoir may directly connect to an applicator element such that a consumer product moves from the reservoir directly to the applicator element. One such example is discussed below with respect to FIG. 17A. In another example, a component of a pumping element may act directly on a consumer product in a reservoir (e.g., a piston in contact with a reservoir and/or inside a reservoir for pushing a consumer product from the reservoir). One such example is discussed below with respect to FIG. 16A.

A device (e.g., device 100, device 200, etc.) may include a mixing chamber to allow combination of one or more consumer products (or components thereof) from multiple reservoirs prior to delivery to an applicator element (e.g., applicator element 120, 220, etc.). Example mixing chambers include, but are not limited to, a chamber that is a separate component, a chamber that is part of a connector, a connector itself, a chamber that is part of a cartridge containing a plurality of reservoirs, and any combinations thereof. In one example, a mixing chamber is positioned between reservoirs 105, 110 and pumping element 115. In another example, a mixing chamber is positioned between pumping element 115 and applicator element 120. In yet another example, a mixing chamber may be a part of a reservoir (e.g., as part of a cartridge). In still yet another example, a mixing chamber may be included without a pumping element (e.g., where manual pressure is applied by a user). In a further example, a mixing chamber may be positioned between a plurality of reservoirs (such as reservoirs 205/210) and an applicator element (such as applicator element 220). Combinations of these examples are also contemplated.

Device 100 is shown with a single in line pumping element 115. In alternative embodiments, pumping element 115 may include multiple components such that two or more of a plurality of reservoirs each include a portion of a pumping element for moving one or more respective consumer products to applicator element 120. In one such example, each pumping element/reservoir combination also includes a separate connection (e.g., such that different consumer products from each reservoir do not combine until a later point, such as at applicator element 120 or a mixing chamber prior to applicator element 120).

Devices 100 and/or 200 may also include one or more consumer product sensors positioned and configured to determine an amount of consumer product remaining in a reservoir and/or an amount of consumer product to be delivered. A consumer product sensor may be a separate component, be part of a pumping element, and/or be integrated with the device in another way. A consumer product sensor may be controlled by a processing element described later. In one example, a consumer product sensor is a combination of one or more pumping element components and a processing element configured to control the one or more pumping element components to provide a specified amount of force predetermined to deliver a specified amount of a consumer product from a reservoir to an applicator element. In another example, a consumer product sensor include a detector component that detects a change in a reservoir that is indicative of a change in an amount of consumer product present in the reservoir. In one such example, a detector component detects a changing level of consumer product by measuring the consumer product directly (e.g., using a light energy to determine a changed distance from the detector component to a surface of the consumer product). In another such example, a detector component detects a change in distance from the detector component to a surface of a piston acting upon a consumer product in a reservoir. Calculations of changed distance may be utilized with other known information (e.g., volume of a reservoir, dimensions of reservoir, etc.) to calculate changes in volume of consumer product. A change in weight may be included in determining a change in amount of consumer product. Example detector components for a consumer product sensor include, but are not limited to, a light energy sensor (e.g., an optical, IR, or other light generating/detecting sensor), a mass measuring component (e.g., a scale circuitry), a weight measuring component, a pressure monitor, and any combinations thereof. A consumer product sensor may also be utilized to provide information about a consumer product, such as product viscosity (e.g., measured with a light detector configured with a processing element to correlate detected physical properties to a particular viscosity). Additionally, a consumer product sensor may also provide information to a processing element to assist it in controlling the delivery of a force via a pumping element (e.g., a light sensor/detector component may measure via changes in distance the speed at which a consumer product is being delivered).

An applicator element, such as applicator element 120, is a structure that is designed and configured to bring one or more consumer products into physical contact with a surface of a user to which the one or more consumer products are to be applied. Example physical contact for applicator element 120 with a surface of a user includes, but is not limited to, manual movement of device 100 by a user to bring applicator element 120 into contact with a surface of the user, automatic movement of applicator element 120 by a mechanism of device 100 (e.g., a motion driving mechanism, discussed further below), manual movement of device 100 in relation to a surface of a user, manual movement of applicator element 120 by a user in relation to a surface of the user, and any combinations thereof.

Applicator element 120 is shown as a single disc-like structure. In other embodiments, applicator element 120 may have a different shape and/or be two or more distinct structures. Alternative shapes for applicator element 120 include, but are not limited to, a sphere, a rectangle, a box, a square, a conical structure, and any combinations thereof. The surface of applicator element 120 used for application may, in one example, include a smooth component. In another example, applicator element 120 may include a textured component. In another example, applicator element may include one or more smooth components and one or more textured components. In one such example, an applicator element may be divided into regions (e.g., 4 pie shaped regions), each with a different texture/smoothness feature. Examples of a textured component may include, but are not limited to, a brush component (e.g., one or more bristles), a textured plastic, a textured fabric, an abrasive surface, a beaded surface, a rippled surface, a pinching texture, and any combinations thereof. In one example, a textured component is removable from an applicator element. In another example, a smooth component is removable from an applicator element. Removability of a component of an applicator element may include, but is not limited to, a snap attachment, a screw attachment, an adhesive (e.g., peel and stick) attachment, a pressure connection, a suction attachment, a tongue and slot attachment, and any combinations thereof. In one example, a removable component of an applicator element is a pad-like structure (e.g., a disposable pad or a reusable pad) that is attachable to a mounting portion of an applicator element. In yet another example, applicator element 120 may include a textured and/or a smooth surface without one or more of the textured and/or smooth portion being a separate component.

Applicator element 120 is shown positioned on a top side of device 100. It is contemplated that applicator element 120 may be mounted to any other side of device 100 as appropriate in other embodiments. Connector 122 is shown connecting pumping element 115 to applicator element 120 for providing one or more consumer products to applicator element 120. Connector 122 may be part of a physical structure that supports applicator element 120 to body 102. In other examples, applicator element 120 may be physically supported to body 102 in other ways. Examples of ways of supporting an applicator element (such as applicator element 120, 220) to a device body (such as body 102, 202) include, but are not limited to, a physical support structure (e.g., a post, a rod, a connector, etc.), an extension of a material of the device body, an adhesive, one or more fasteners, and any combinations thereof. Example ways for a connector (e.g., connector 122, 222) to provide a consumer product to a surface of an applicator element (e.g., applicator element 120, 220) include, but are not limited to, via an opening in applicator element allowing the connector (e.g., a conduit) to pass at least partially through the applicator element for the consumer product to be delivered to an outer surface of the applicator element, via a sponge-like termination to the connector that forms a portion of the applicator element, via a screen-like termination to the connector that forms a portion of the applicator element, via a porous component of the applicator element that comes into contact with an end of the connector, other junctures between a connector and an applicator element, and any combinations thereof. As discussed above, a reservoir may contact directly to one or more applicator elements to provide a consumer product directly to the applicator element.

Applicator element 120 itself (or in conjunction with a textured and/or smooth component) may be removable from device 100. Example mechanisms for providing removability of applicator element 120 include, but are not limited to, a snap attachment, a screw attachment, an adhesive (e.g., peel and stick) attachment, a pressure connection, a suction attachment, and any combinations thereof. Applicator element 120 itself and/or a textured and/or smooth component may be made of any material sufficient for the purposes of applying a desired consumer product. Example materials for an applicator element or component thereof include, but are not limited to, a plastic, a metal, a rubber, a silicon molded part, a glass, a pressurized aluminum, a foam, a sponge, and any combinations thereof.

As discussed above, applicator element 120 may be moveable with respect to device 100. Movement of applicator element 120 and of device 100 (e.g., with respect to the surface to which one or more consumer products are to be applied) can improve the application of a consumer product (e.g., via improved physical application, via improved absorption into the surface, via agitation of the surface, such as via exfoliation, etc.) and/or improve surface treatment physically (e.g., via exfoliation, via massage, etc.). Motion of applicator element 120 can be of the entire applicator element, one or more portions thereof (e.g., a multi-surface applicator element 120 having each surface move in conjunction with each other and/or independently), or both. For example, applicator element 120 may include three disc-like components (e.g., textured pads) within an overall disc shaped applicator element in which the three disc-like components each move (e.g., rotate) and the overall disc shaped applicator element also moves (e.g., rotates) with respect to device 100. Example movements with respect to device 100 include, but are not limited to, a rotary motion, an articulating motion, a pulsing motion, a sonic motion, a tilt motion, a motion in and out of an axis perpendicular to device 100, a motion side-to-side with respect to device 100, a motion top-to-bottom with respect to device 100, and any combinations thereof. In one example, an applicator element rotates. To effect motion, device 100 and applicator element 120 may be connected via a moveable connection and include a motion driving mechanism that includes components that allow a desired movement. Example connection and motion driving mechanism components include, but are not limited to, a hinge, a socket, a joint, an articulating element, a rotating axis, a motor with a rotational movement, a motor with lateral movement, a motor with a sonic movement, a motor with a vibrating movement, a motor with a hammer/pulsing movement, and any combinations thereof. Various motors (including micro-motors) are known for providing multiple types of movement. Example embodiments including a motion driving mechanism are discussed below with respect to FIGS. 3 and 4. In an example that does not include a motor, movement of applicator element 120 may be effectuated by manual movement of device 120 and/or applicator element 120 by the user. In another example, a device may include two or more applicator elements (and/or a single applicator element with multiple different subcomponents) in which a subset of applicator elements have automated movement functionality and a subset of applicator elements do not have automated movement functionality.

In one example, a connection of applicator element 120 to device 100 may include both a connection for physical movement and a connection for providing one or more consumer products from one or more reservoirs 105, 110. In one such example, an axis for movement may be hollowed to allow a conduit for one or more consumer products.

As discussed above, multiple reservoirs 105, 110 allow for intelligent functionality in application of consumer products to a surface of a user (such as sequential application, component mixing, etc.). Device 100 may include a processing element for controlling intelligence of device 100, including action of pumping element 115, action of applicator element 120, combinations of consumer products, sequences of consumer product application (e.g., differing by time of day, such as at night applying a cleaner first and then a facial mask in sequence), dosages of consumer product application, communications with remote devices and/or locations, consumer product supply management, identification of a consumer product in a reservoir of device 100, identification of data regarding a consumer product in a reservoir of device 100 (e.g., an expiration date, a prescribed dosage, etc.), identification of information regarding a cartridge inserted as part of a reservoir of device 100, a volume of a reservoir of a cartridge, and indication of remaining consumer product, maintaining historical data for one or more users of device 100 (e.g., time, date, dosage, scheduling of applications, durations of applications, etc. for each user), information for a user of device 100 on prescription instructions (e.g., dosing, duration, frequency, etc.), an alert to a user as to missing a scheduled application, notification to a user regarding compliance with a schedule and/or prescription, and other aspects and features of a device according to the current disclosure. Examples of such intelligent aspects and features are discussed in the example implementations and embodiments above and those discussed below. Example processing elements include, but are not limited to, a microprocessor, a microcontroller, one or more static programmed circuits (e.g., fixed circuitry programmed for one or more tasks), a programmable integrated circuit (PIC), ASIC, and any combinations thereof.

A processing element may include (and/or be associated with a separate) memory element for storing one or more instructions related to a functionality and/or feature of device 100. A memory element may also store data and information about device 100, a cartridge in device 100, a desired consumer product (e.g., prescribed dosage information), a connected remote device, and/or any other information used in the operation of device 100. In one example, device 100 includes a processing element with an included memory element. In another example, device 100 includes a memory element separate from a processing element. In yet another example, device 100 includes a processing element with an included memory element and a memory element separate from the processing element. A memory element may be electrically connected to a processing element for communication between the two elements.

Device 100 may also include an external connector (not shown in FIG. 1). External connector may be connected to internal components of device 100 to provide connectivity to an external device, an external power supply, and/or other components external to device 100. Example internal components of device 100 for connection to an external connector include, but are not limited to, a processing element, a power supply, a memory element, a display element, a user interface, a user input element, a network functionality, and any combinations thereof. Example external connectors include, but are not limited to, a network connector, a power connector, a data connector, and any combinations thereof. In one example, device 100 includes multiple external connectors (e.g., each with one or more functionalities). In another example, device 100 includes a single external connector with multiple functionalities (e.g., a data connector and power connector in one port). Example network connectors include, but are not limited to, a serial network connector, an Ethernet connector, a LAN (local area network) connector, a WAN (wide area network) connector, an RJ45 connector, a USB connector (Universal Serial Bus), a proprietary network connector, a mini jack connector, and any combinations thereof. Device 100 may include network circuitry (e.g., network adaptor circuitry, such as Ethernet circuitry) in communication with an external connector including a network connector. Such network circuitry may also be in electrical communication with a processing element and/or a power supply of device 100. Example power connectors include, but are not limited to, a USB connector, a proprietary power connector, a mini jack connector, an induction power transfer connector (e.g., an induction coil inside body 102 that provides an induction connection to an external induction coil, such as a coil in a docking station and/or cradle), and any combinations thereof. Example data connectors include, but are not limited to, a USB connector, a FireWire connector, a serial connector, a proprietary data connector, a mini-jack connector, and any combinations thereof. Device 100 may utilize an external connector for a variety of reasons. Example uses for an external connector include, but are not limited to, updating information in a memory of device 100 (e.g., updating firmware, software, data for dosing, etc.), providing new functionalities to device 100 (e.g., via data/instruction import, firmware upgrade etc.), charging an internal power supply of device 100, connecting device 100 to an external power supply, connecting device 100 to a network, connecting device 100 to one or more remote locations and/or devices, connecting device 100 to a docking station and/or cradle, and any combinations thereof.

Device 100 may also include a wireless communication functionality in place of (or in addition to) an external network connector. Example uses for a wireless communication functionality include, but are not limited to, transferring data and/or information from device 100 to a remote device and/or location, transferring data and/or information from a remote device and/or location to device 100, connecting device 100 to a network, connecting device 100 to a remote device and/or location, updating a firmware and/or software of device 100, connecting device 100 to a docking station/cradle that itself has a wireless communication functionality, and any combinations thereof. Example wireless communication functionalities include, but are not limited to, a radio frequency wireless network circuitry, an optical wireless network circuitry (e.g., an infrared network circuitry, including an optical receiver/transmitter), a Bluetooth circuitry, a WiFi standard circuitry, and any combinations thereof. Device 100 may include an antenna (e.g., an internal antenna, an external antenna) as part of a wireless communication functionality and/or as an associated (electrically connected) component to a wireless communication functionality. Example networks are discussed further below.

As discussed above, device 100 may include a power supply. Any power supply capable of providing the components of device 100 with the required power for operation is sufficient for inclusion with device 100. A power supply may be internal to body 102. In one such example, an internal power supply is not configured for removal from body 102 by an ordinary user (e.g., without taking body 102 physically apart). In another such example, an internal power supply is configured for removal from body 102 by an ordinary user (e.g., body 102 is provided with an opening for insertion and removal of a power supply, body 102 is provided with a removable connector for mounting a power supply to be conformally part of body 102, etc.). A power supply may also be wholly or partially external to body 102. Example power supplies include, but are not limited to, a battery, a removable power source, a rechargeable power source, a capacitor, a fuel cell, a wired connection to an external battery or other power source (e.g., a wall outlet, AC adapter), an induction coil power supply element, and any combinations thereof. Device 100 can include appropriate electrical connections between a power supply and internal components requiring power.

Device 100 may include (and/or be associated with) one or more user interfaces for use by a user in interacting with device 100. Example user interfaces include, but are not limited to, a user input element (e.g., a button, a dial, a control switch, etc.), an output element, a visual indicator (e.g., an LED), a display screen (e.g., a static display, an LCD, a touch screen capable of user interaction, etc.), a microphone, a haptic output (e.g., a vibration circuitry configured to provide a vibration sensation to the device), an audio output (e.g., a speaker, other audio producing circuitry), and any combinations thereof. A user interface may be part of device 100 (e.g., as an external interface). Several example user interfaces on a consumer product applicator device are discussed further below with respect to FIG. 5. In addition to a user interface element on device 100 (or in place of such elements), device 100 may be associated with one or more other devices (e.g., a remote user device, a separate display screen, a docking station/cradle, etc.) that have one or more interface elements that can be used by a user to interface with device 100. Associations of device 100 with other devices can be provided in a variety of ways including, but not limited to, via an external network connection, an external data connection, a wireless communication functionality, a network, direct mounting into a docking station/cradle, and any combination thereof. An example of a docking station embodiment is discussed further below with respect to FIG. 6. Example remote devices are discussed further below with respect to FIG. 7. One exemplary advantage to interfaces on a remote device includes the ability to take advantage of more sophisticated (e.g., higher definition screens, touch screens, greater processing power, connection to the Internet, etc.) features of some remote devices than may be practical to include directly on device 100 in a particular implementation (e.g., small, portable embodiments; lower cost variations, etc.).

A user input such as a microphone may be connected with a processing element (and corresponding machine executable instructions) for providing a voice recognition capability. In such an example, a user of device 100 (or another device according to this disclosure) could provide voice prompts to provide control and/or other instruction to the device.

One or more device outputs can be used to provide signals and other information to a user of the device. Example signals may be alerts (discussed throughout this disclosure). Example user signals may include, but are not limited to, a haptic signal, an audio signal, a textual information, a visual indication (e.g., a blinking LED), a graphical information, and any combinations thereof.

Device 100 may optionally include a light generating element and corresponding light generating circuitry (e.g., controlled by a processing element) (not shown). The light output intensity and/or light output frequency may be chosen and configured to correspond to one or more activation energies required for a consumer product to be applied with a device. Such a light generating element may be positioned on a device to provide light to a surface of a subject at the same time as application of a consumer product and/or at a different time (e.g., shortly after application).

A consumer product may be designed to be applied at one or more temperatures. For example, a consumer product may be cooled prior to application. In another example, a consumer product may be heated prior to application. Heating and/or cooling a consumer product may be accomplished by a user externally to device 100. Device 100 may also include one or more circuitries and/or components for heating and/or cooling a consumer product prior to application.

Figure 3:
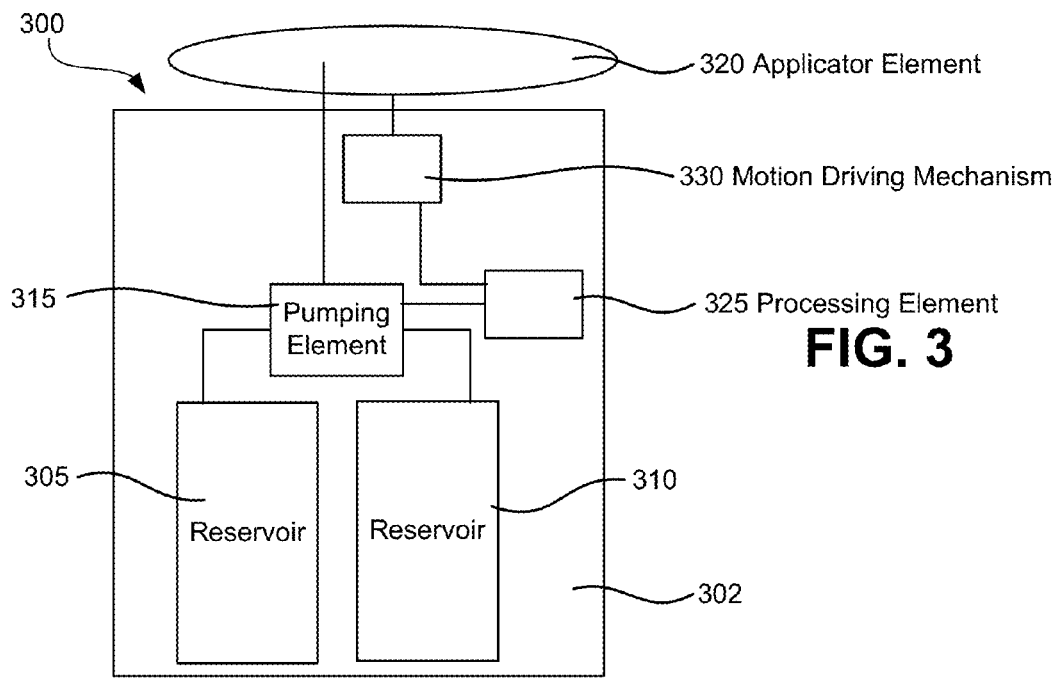
FIG. 3 illustrates a cross sectional view of still another exemplary implementation of a device for application of one or more consumer products.

FIG. 3 illustrates a cross sectional view of still another exemplary implementation of a device 300 for application of one or more consumer products to a surface of a user. For purposes of efficient disclosure, components of device 300 that are similar to those of device 100 and/or 200 may have similar features, aspects, functionalities, options, and alternatives as those discussed above with respect to device 100 and/or 200 (including the ability for optional components that are not shown in FIG. 1, but are discussed therein), except where described in a contrary fashion with respect to device 300. Additional features, aspects, functionalities, options, and alternatives may be discussed with respect to a like component of device 300, and are contemplated to be applicable (where not contrary to the discussion above) to the like components of device 100 and/or 200.

Device 300, having a body 302, includes a reservoir 305 and a reservoir 310 connected to a pumping element 315 (e.g., via conduit), which is further connected (e.g., via conduit) to an applicator element 320. Device 300 also includes a processing element 325 in electrical communication with pumping element 315 for controlling the delivery of one or more consumer products from one or more of reservoirs 305, 310 to applicator element 320 and for other operation of components of device 300. Device 300 also includes a motion driving mechanism 330 in electrical communication with processing element 325 and including physical connection to application element 320 for providing one or more motion features to application element 320. Various motion features and components of a motion driving mechanism are discussed above.

Figure 4:
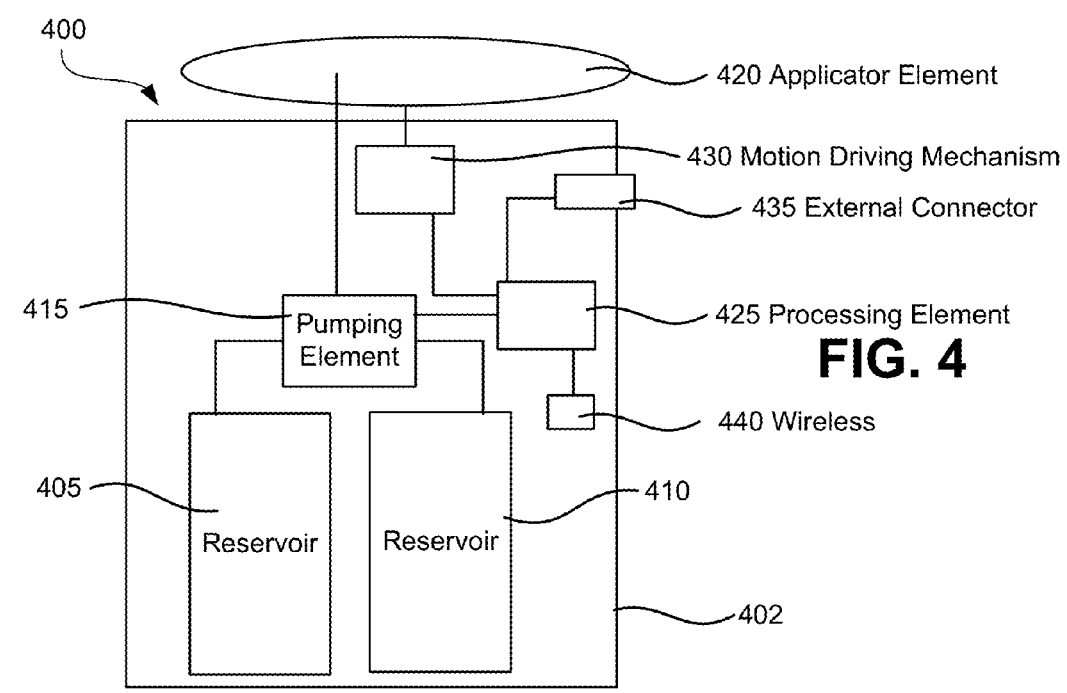
FIG. 4 illustrates a cross sectional view of yet another exemplary implementation of a device for application of one or more consumer products.

FIG. 4 illustrates a cross sectional view of yet another exemplary implementation of a device 400 for application of one or more consumer products to a surface of a user. For purposes of efficient disclosure, components of device 400 that are similar to those of device 100 and/or 200 may have similar features, aspects, functionalities, options, and alternatives as those discussed above with respect to device 100 and/or 200 (including the ability for optional components that are not shown in FIG. 1, but are discussed therein), except where described in a contrary fashion with respect to device 400. Additional features, aspects, functionalities, options, and alternatives may be discussed with respect to a like component of device 400, and are contemplated to be applicable (where not contrary to the discussion above) to the like components of device 100 and/or 200.

Device 400, having a body 402, includes a reservoir 405 and a reservoir 410 connected to a pumping element 415 (e.g., via conduit), which is further connected (e.g., via conduit) to an applicator element 420. Device 400 also includes a processing element 425 in electrical communication with pumping element 415 for controlling the delivery of one or more consumer products from one or more of reservoirs 405, 410 to applicator element 420. Device 400 also includes a motion driving mechanism 430 in electrical communication with processing element 425 and including physical connection to application element 420 for providing one or more motion features to application element 420. Various motion features and components of a motion driving mechanism are discussed above.

Device 400 further includes an external connector 435 in electrical communication with processing element 425 for providing one or more connections to device 400 to an external element via external connector 435. In one such example, processing element 425 may utilize information in a memory element to control the operation of external connector 435, manage power input via external connector 435 (e.g., to one or more components of device 400 and/or to an internal power supply of device 400), update information of a memory element using information from an external source via external connector 435, manage a network connection, connect processing element 425 to one or more user interfaces of a remote device and/or docking station/cradle, control the application of one or more consumer products from reservoirs 405/410 (e.g., control dosing, control amounts of combinations of products and/or components thereof, control sequence of application of consumer products and/or components thereof, etc.) using information via external connector 435 (e.g., information from a remote user device with user interface), and/or perform one or more other functions utilizing external connector 435.

Device 400 includes a wireless communication functionality 440 in electrical communication with processing element 425. Exemplary functionalities for a wireless communication functionality are discussed above.

Figure 5:
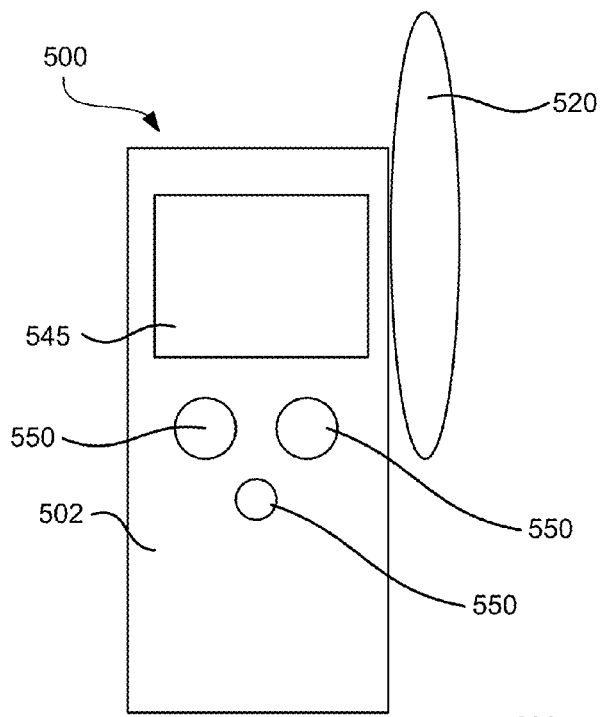
FIG. 5 illustrates an exterior side view of one exemplary implementation of a device for application of one or more consumer products.

FIG. 5 illustrates an exterior side view of one exemplary implementation of a device 500 for application of one or more consumer products to a surface of a user. While not shown, device 500 may include any of the components (their features, options, functionalities, and alternatives) as discussed with respect to device 100, 200, 300, and/or 400 above. Device 500 includes a body 502 and an applicator element 520. On the exterior of body 502 is shown the exterior portions of a display screen user interface 545 (e.g., a touch screen, an LCD, etc.) and multiple user control interfaces 550 (e.g., buttons, knobs, etc.) for allowing a user to interact with device 500. Display screen user interface 545 and user control interfaces 550 are connected internally to a processing element (not shown) for allowing a user to make input via control interfaces 550 and/or screen 545 and to receive information regarding the operation of device 500 via screen interface 545.

Figure 6:
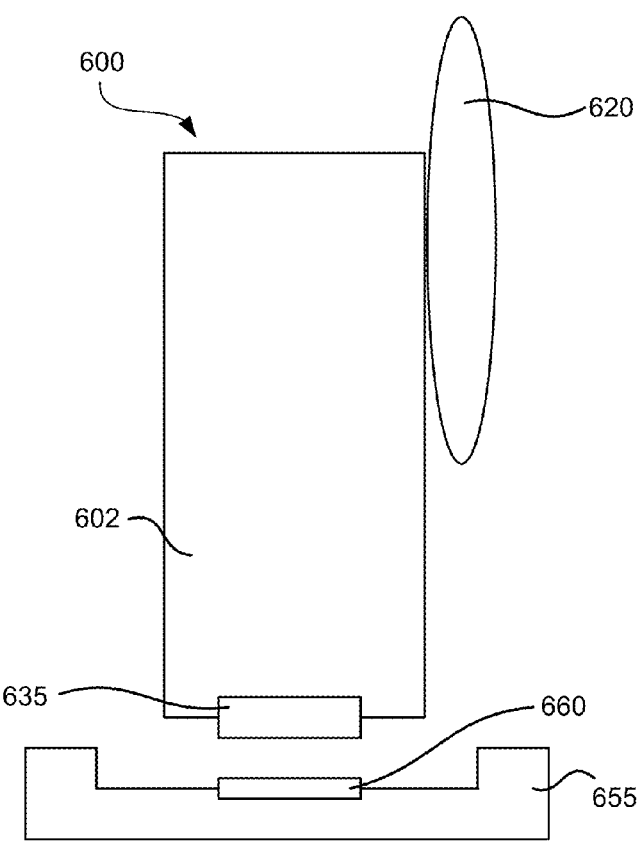
FIG. 6 illustrates an exterior side view of another exemplary implementation of a device for application of one or more consumer products.

FIG. 6 illustrates an exterior side view of another exemplary implementation of a device 600 for application of one or more consumer products to a surface of a user. While not shown, device 600 may include any of the components (their features, options, functionalities, and alternatives) as discussed with respect to device 100, 200, 300, 400, and/or 500 above. Device 600 includes a body 602 and an applicator element 620. An external connector 625 is connected to a processing element (not shown) internal to body 602. In one example, body 602 is configured to be mountable with a docking station/cradle 655. In another example, external connector 625 is configured to be connectable to a connector 660 of docking station/cradle 655. In yet another example, body 602 is configured to be mountable (e.g., via a pressure connection, via a conformal fit, via a snap connection, etc.) with docking station/cradle 655 and external connector 625 is configured to be connectable to connector 660. Docking station/cradle 655 may include a display device and/or other user interface controls. In another example docking station/cradle 655 may be configured to have a display device removably attached to the docking station/cradle to allow for expanded user interface options (e.g., when device 600 is attached to the docking station/cradle 655 and/or when device 600 is remotely connected to docking station/cradle 655). Such a display device can provide any of the information related to the operation of device 600 that is discussed throughout this disclosure including, but not limited to, current date/time (e.g., to alert a user to a scheduled application), scheduling information for application, information about device 600, information about one or more consumer products for application by device 600, information about one or more cartridges connected to device 600, prescription information, other operating information, and any combinations thereof. Such information is the same as may be displayed by a display element on device 600 or displayed by an app on a connected user computer device. Docking station/cradle 655 may include a power supply and/or be connected to an external power supply (e.g., via a wired connection to a wall outlet) to provide power to device 600 via external connector 625 and connector 660. In one example, external connector 625 and connector 660 include inductive elements that allow passage of power via the inductive elements. Docking station/cradle 655 may include a wireless communication functionality for wireless networking with device 600.

As discussed above, a device (such as device 100, 200, 300, 400, 500, and/or 600) for application of one or more consumer products to a surface of a user ("an applicator device") may be connected via a wired and/or wireless connection to a network for connecting the applicator device to a remote device and/or location. Example networks include, but are not limited to, a wide area network (e.g., the Internet, an enterprise network), a local area network (e.g., an Ethernet network, a WiFi network), a telephone network, a data network associated with a telephone/voice provider, a direct connection between two computing devices (e.g., a wired connection and/or a wireless connection), a near-field wireless connection between two devices (e.g., a Bluetooth connection), and any combinations thereof. Example remote devices include, but are not limited to, a laptop computer, a desktop computer, a personal data assistant (PDA), a smartphone, a portable computing device, a server computer, a computer workstation, a terminal computer, a server computer, a handheld device (e.g., a tablet computer, a personal digital assistant "PDA", a mobile telephone, etc.), a web appliance, a network router, a network switch, a network bridge, any machine capable of executing a sequence of instructions that specify an action to be taken by that machine, a docking station/cradle, and any combinations thereof. A remote device may be located at a variety of locations having a value to be connected to an applicator device according to the present disclosure. Example locations for a remote device include, but are not limited to, in close proximity to the user using an applicator device, at a supplier of one or more replacement parts for the applicator device, at a supplier of one or more consumer products for application by the applicator device, at a supplier of a cartridge having one or more consumer products for application by an applicator device, at a manufacturer of an applicator device, at a retailer of an applicator device, at a pharmacy capable of filing a prescription for one or more consumer products to be applied by the applicator device, at a location of a physician (e.g., a physician providing advice related to treatment with the applicator device, a physician capable of providing new and/or renewed prescriptions for one or more consumer products to be applied with the applicator device), at a location of a service provider associated with an applicator device (e.g., a beauty consultant/coach, a sales agent), at a location of a service provider associated with one or more consumer products for an applicator device (e.g., a beauty consultant/coach, a sales agent), and any combinations thereof.

A remote device may include one or more sets of machine executable instructions that are executable by the remote device (e.g., instructions stored on a memory and executable using one or more processing elements) for allowing a user of the remote device to have one or more interactions with an applicator device of the present disclosure. Example interaction for a remote device with an applicator device includes, but is not limited to, viewing data provided by the applicator device, receiving instructions to be provided to the applicator device, providing a user with performance information of the applicator device, providing a user with historical information of one or more consumer products applied using the applicator device, providing a user with one or more alerts related to the operation of the applicator device, providing a user with a schedule of desired applications of one or more consumer products using the applicator device, providing a user with an interface to schedule desired applications of one or more consumer products using the applicator device, providing a user with an interface for inputting a prescription for one or more consumer products using the applicator device, providing a pharmacist with a prescription renewal request, providing a doctor with a prescription renewal request, providing a subscription service provider of refills of one or more consumer products for application with the applicator device with a request for one or more refills, providing an updated schedule for application, providing an updated sequence for application, providing updated mixing instructions, providing updated dosages for application, and any combinations thereof.

Example alerts include, but are not limited to, an indication to a user of an applicator device that an error in the device has occurred (e.g., a part needs to be replaced), an indication indicator that an incorrect cartridge has been installed in the applicator device (e.g., an incorrect consumer product is present in the applicator device for a desired schedule of application), an indication of a level of a consumer product in a reservoir, an indication of a compliance and/or deviation from a prescription, an indication that a component of an applicator element is worn out, an indication of a recall that has been issued for the device (e.g., sent to the device from a manufacturer), an indication of a recall that has been issued for one or more consumer products (e.g., sent to the device from a provider of the consumer product), another type of alert to a condition of operation of an applicator device, and any combinations thereof.

In one example, a prescription is a formal legal prescription provided by a medical provider in which the prescription is usually filled by a pharmacist or dispensed by another official authorized to dispense controlled substances. In another example, a prescription is an less formal instruction for one or more consumer products that may not be regulated by a government body such that it requires dispensing by a pharmacist or other official. Example information in a prescription includes, but is not limited to, identification of one or more consumer products for application, identification of a dosage, identification of a schedule for application (e.g., how often to apply), identification of combination amounts for combining two or more components of a consumer product and/or two or more consumer products, and any combinations thereof.

In one example, an applicator device connects to a user's personal computing device (e.g., a laptop, a smartphone, a tablet, etc.) to provide a user interface for the applicator device. In one such example, the user's personal computing device can run a software application ("an app") that is configured as machine executable instructions to provide specialized interaction with the applicator device.

In another example, an applicator device connects to a remote device at manufacturer or other supplier to provide a connection for updates to firmware, software, and other information from the manufacturer or other supplier. In one such example, an update may be initiated by the remote user and/or by a user of the applicator device (e.g., via an app on a connected smartphone). For example, a user of an applicator device may receive a text, an alert, or another indication that a new version of a firmware, a software, or other information for operating the applicator device is available. The user could then initiate a transfer of the firmware, software, or other information. In another such example, performance information from an applicator device may be transferred via a network to a device at a manufacturer or other supplier (e.g., via an app on a user's smartphone or other user computing device). Such performance data may be used to verify the correct operation of the applicator device and/or detect problems (in which case an update of firmware, software, or other information may be initiated and/or an alert or other message may be sent to the user of the applicator device to take an action, such as return the device for service). In one such example, an alert may include an indication or safety alert that an incorrect cartridge is installed, a cartridge is installed incorrectly, or that a cartridge is empty. Other notices may include indications that a recall has been issued for the device and/or one or more consumer products.

A remote device may also include videos and/or audio information for providing instructions to a user on the operation, functionality, and other aspects of an applicator device according to this disclosure. A remote device display element may be utilized for this purpose. For example, a virtual reality display element may allow user to view such a video and/or audio information.

Figure 7:
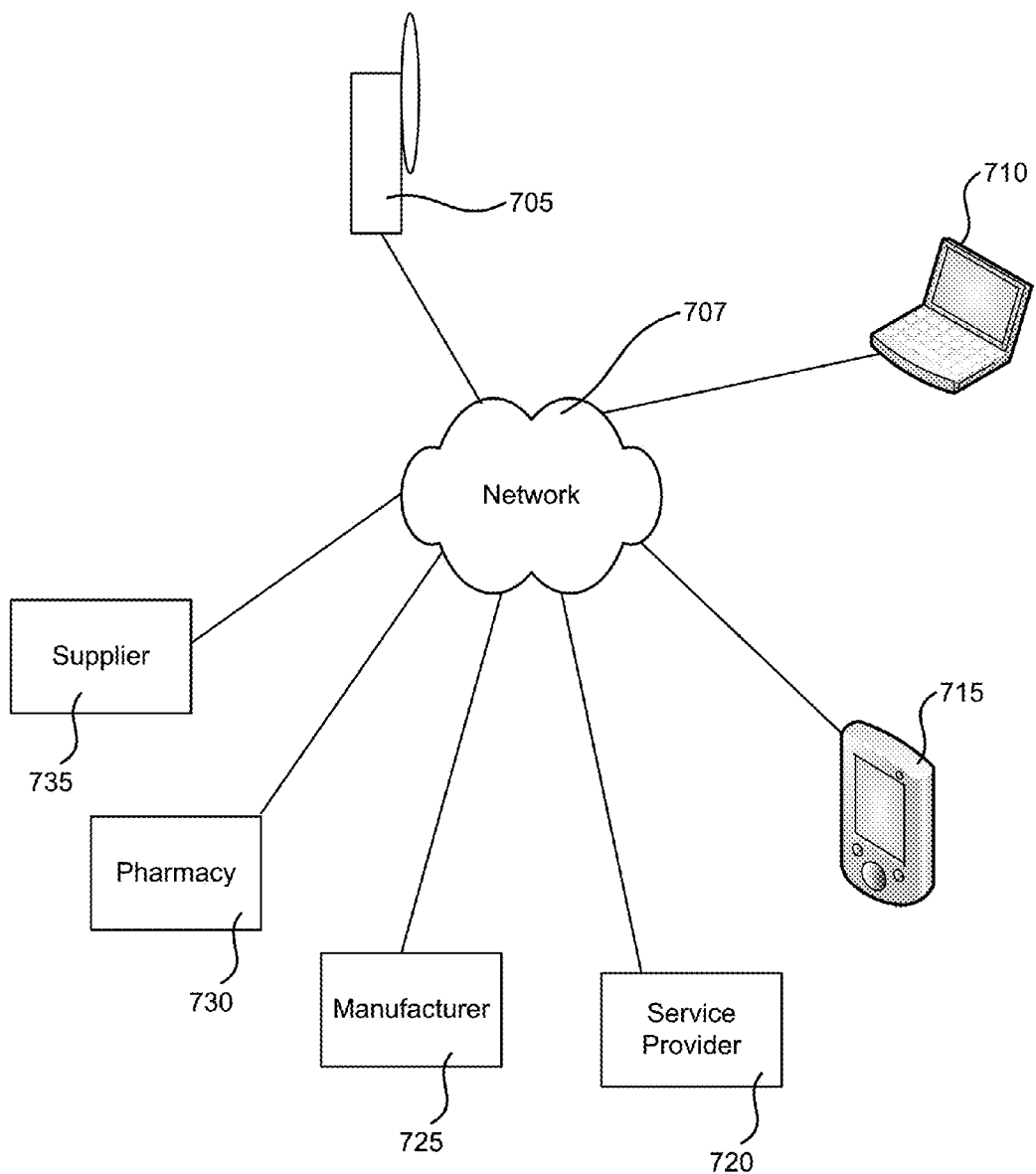
FIG. 7 illustrates an exemplary implementation of a networking environment.

FIG. 7 illustrates an exemplary implementation of an applicator device 705 connected via a network 707 to a laptop computer 710, a smartphone 715, a device at a service provider 720, a device at a manufacturer 725, a device at a pharmacy 730, and a device at a supplier 735.

Figure 8A:
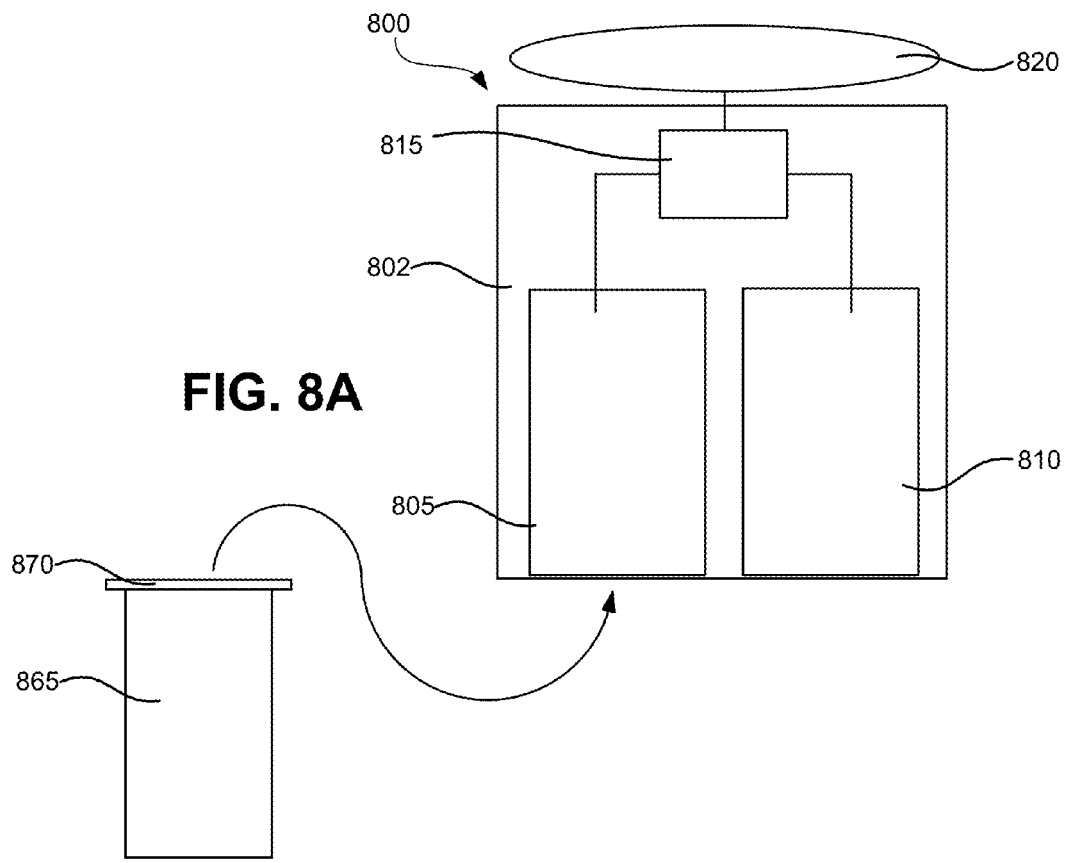
FIG. 8A illustrates a cross sectional view of one exemplary implementation of a device for application of one or more consumer products with at least one of the one or more consumer products supplied via a removable cartridge.
Figure 8B:
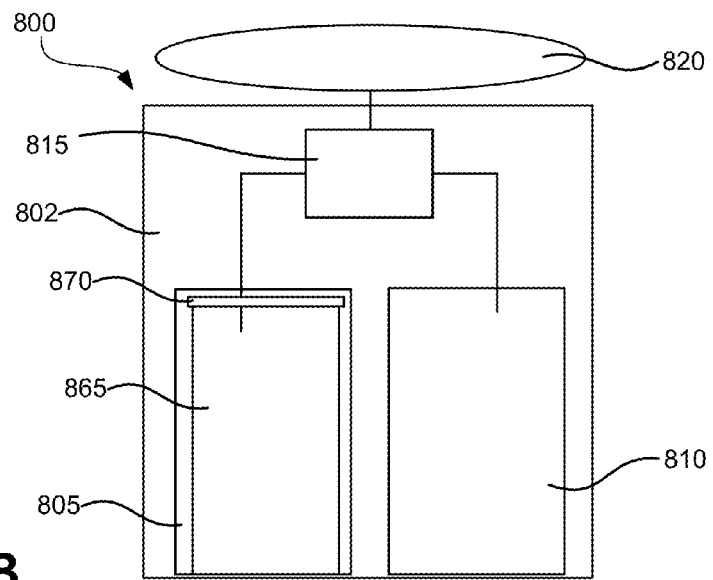
FIG. 8B illustrates another cross sectional view of the device of FIG. 8A.

FIGS. 8A and 8B illustrate a cross sectional view of one exemplary implementation of a device 800 for application of one or more consumer products to a surface of a user with at least one of the one or more consumer products supplied via a removable cartridge 865. For purposes of efficient disclosure, components of device 800 that are similar to those of device 100 have similar features, aspects, functionalities, options, and alternatives as those discussed above with respect to device 100 (including the ability for optional components that are not shown in FIG. 1, but are discussed therein), except where described in a contrary fashion with respect to device 800. Additional features, aspects, functionalities, options, and alternatives may be discussed with respect to a like component of device 800, and are contemplated to be applicable (where not contrary to the discussion above) to the like components of device 100.

Device 800 includes receptacles 805 and 810, each of which is configured to receive a removable reservoir cartridge (such as cartridge 865) to form one or more reservoirs for holding one or more consumer products using device 800. As discussed above, each cartridge 865 may include one or more reservoirs. Device 800 is also shown with a pumping element 815 and an applicator element 820. As mentioned, device 800 may include any of the additional components discussed above as is appropriate for a given implementation.

Removable cartridge 865 includes a cover 870 enclosing a reservoir within the cartridge. Cover 870 allows one or more consumer products within cartridge 865 to remain in cartridge 865 until use. In one example, cover 870 is removable before insertion in one of receptacles 805, 810. In another example, cover 870 remains on cartridge 865 when inserted in one of receptacles 805, 810. In one such example, one or more connections to pumping element 815 includes a configuration for insertion through cover 870 to access one or more reservoirs therein. Example configuration for insertion through cover 870 include, but are not limited to, cover 870 being made of a puncturable material (e.g., a foil) and the connection to pumping element 815 including a structure for puncturing the material and providing a connection that allows delivery of one or more consumer products therein to applicator element 820, cover 870 including a connection to which a connector to pumping element 815 can insert to allow access to one or more consumer products therein, and any combinations thereof. FIG. 8B shows cartridge 865 inserted into an opening in the bottom of receptacle 805 and placed into receptacle 805. Cover 870 remains and is punctured via a structure of the connector to pumping element 815. In one example, cartridge 865 is configured to be disposable after one or more uses in device 800. In another example, cartridge 865 is configured to be used repetitively with refilling by a user and/or a service provider. Receptacles 805, 810 and associated connectors to pumping element 815 may be cleaned upon removal of cartridge 865.

Figures 9A, 9B:
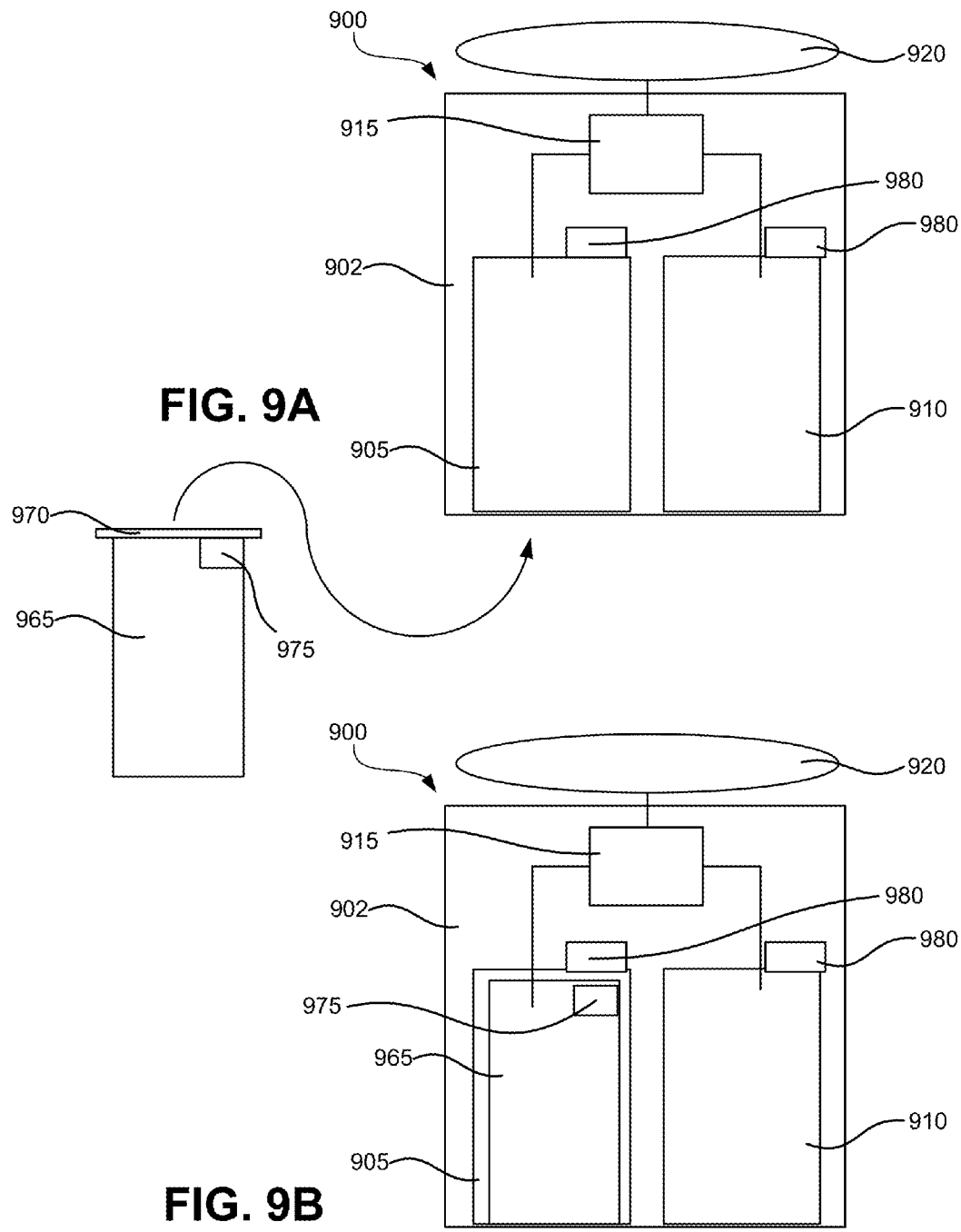
FIG. 9A illustrates a cross sectional view of another exemplary implementation of a device for application of one or more consumer products with at least one of the one or more consumer products supplied via a removable cartridge.
FIG. 9B illustrates another cross sectional view of the device of FIG. 9A.

FIGS. 9A and 9B illustrate a cross sectional view of another exemplary implementation of a device 900 for application of one or more consumer products to a surface of a user with at least one of the one or more consumer products supplied via a removable cartridge 965. For purposes of efficient disclosure, components of device 900 that are similar to those of devices 100 and 800 have similar features, aspects, functionalities, options, and alternatives as those discussed above with respect to devices 100 and 800 (including the ability for optional components that are not shown in FIG. 1, but are discussed therein), except where described in a contrary fashion with respect to device 900. Additional features, aspects, functionalities, options, and alternatives may be discussed with respect to a like component of device 900, and are contemplated to be applicable (where not contrary to the discussion above) to the like components of devices 100 and 800.

Device 900 includes receptacles 905 and 910, each of which is configured to receive a removable reservoir cartridge (such as cartridge 965) to form one or more reservoirs for holding one or more consumer products using device 900. As discussed above, each cartridge 965 may include one or more reservoirs. Device 900 is also shown with a pumping element 915 and an applicator element 920. As mentioned, device 900 may include any of the additional components discussed above as is appropriate for a given implementation.

Removable cartridge 965 includes a cover 970 enclosing a reservoir within the cartridge. Cover 970 allows one or more consumer products within cartridge 965 to remain in cartridge 965 until use. In one example, cover 970 is removable before insertion in one of receptacles 905, 910. In another example, cover 970 remains on cartridge 965 when inserted in one of receptacles 905, 910. In one such example, one or more connections to pumping element 915 includes a configuration for insertion through cover 970 to access one or more reservoirs therein. Example configuration for insertion through cover 970 include, but are not limited to, cover 970 being made of a puncturable material (e.g., a foil) and the connection to pumping element 915 including a structure for puncturing the material and providing a connection that allows delivery of one or more consumer products therein to applicator element 920, cover 970 including a connection to which a connector to pumping element 915 can insert to allow access to one or more consumer products therein, and any combinations thereof. FIG. 9B shows cartridge 965 inserted into an opening in the bottom of receptacle 905 and placed into receptacle 905. Cover 970 has been removed and a structure of the connector to pumping element 915 is inserted therein. In one example, cartridge 965 is configured to be disposable after one or more uses in device 900. In another example, cartridge 965 is configured to be used repetitively with refilling by a user and/or a service provider.

Cartridge 965 includes an identification element 975 and device 900 includes one or more identification reader elements 980 positioned to be able to read an identification element 975 when a cartridge, such as cartridge 965 is placed in a receptacle 905, 911. Identification element 975 includes information about cartridge 965, the one or more reservoirs therein, and/or one or more consumer products therein. Example identification elements include, but are not limited to, an RFID device (e.g., an RFID chip), an optical identification mechanism (e.g., a bar code), a mechanical element (e.g., a physical structure, such as a key), and any combinations thereof. An identification reader element 980 can be selected to match a particular type of identification element used by cartridges configured to be placed in device 900 (e.g., an RFID reader circuitry matched to an RFID chip, an optical reader matched with a bar code, a physical slot designed to accept a physical key structure on a cartridge, etc.). An identification reader element 980 may be in electrical communication with a processing element of device 900 for allowing control of reader element 980 and/or processing of information read from identification element 975.

Identification element 975 may include any information that can assist device 900 with utilizing one or more consumer products from cartridge 965. Example information that can be stored on an identification element of a removable cartridge and/or be read by an applicator device includes, but is not limited to, a volume of one or more consumer products within a reservoir of a cartridge, information identifying one or more consumer products within a reservoir of a cartridge, a sequence instruction for application of two or more consumer products in a given order, a prescription for a consumer product, an instruction of a dosage of a consumer product for application, a schedule of one or more applications of a consumer product, a concentration of a consumer product, an instruction for combining one or more consumer products (and/or components thereof) prior to delivery to an applicator element, an instruction for combining one or more consumer products (and/or components thereof) at the time of deliver to an applicator element, and any combinations thereof. An identification element may share components with or be the same element as a consumer product sensor (discussed above). A device (such as device 100, 200, 300, 400, 500, 600, 800, 900, 1500, 1600, 1700) may include one or more components configured to provide the functionality of an identification element (such as identification element 975) and a consumer product sensor.

Receptacles 805, 810 are shown configured to provide for a cartridge to be inserted within body 802 and receptacles 905, 910 are shown configured to provide for a cartridge to be inserted within body 902. In an alternative implementation, a connection to a pumping element (or a connection directly to an applicator element or a mixing chamber, such as when a user can manually provide pressure to a cartridge to force one or more consumer products to be delivered) can be made such that a cartridge is wholly and/or partially external to a body of an applicator device. In one such example, a receptacle may not be provided and an applicator device may include a connector on an external surface of the device. Example ways for a cartridge for a for a cartridge, such as cartridges 865, 965, to connect to an applicator device include, but are not limited to, a screw connection, a snap connection, a pressure connection, a puncture connection, a tube connection, a gasketed connection, and any combinations thereof.

FIG. 10 illustrates an exterior view of one exemplary implementation of a removable cartridge 1005 having one or more reservoirs for holding one or more consumer products and attachment to an applicator device such as any of those described herein. Removable cartridge 1005 includes a main body portion and a passageway 1010 to an opening covered by removable cover 1015. In one example passageway 1010 is a cylindrical shape and cover 1015 is a screwable plug-like cover that can be removed by rotation from the opening at the top of passageway 1010. Passageway 1010 connects to one or more reservoirs within cartridge 1005. In one example, two or more reservoirs connect to passageway 1010. In one such example, passageway 1010 is a singular passageway in which consumer products from each of the two or more reservoirs pass to the opening in passageway 1010 to a connector of an applicator device (for delivery to an applicator element). In another such example, passageway 1010 includes a plurality of separated passageways, each connected to a different reservoir within cartridge 1005, such that a consumer product from each reservoir can pass to the opening of passageway 1010 and to an applicator device without combining with others. In an alternative implementation (not shown), cartridge 1005 may include a mixing chamber configured to receive a consumer product from each of two or more reservoirs within cartridge 1005 prior to the combined mixture of consumer products being delivered to an applicator element of an applicator device via the opening in passageway 1010. A removable cartridge, such as cartridge 1005, cartridge 965, cartridge 865, etc., may be constructed of any of a variety of materials. In one example, a removable cartridge is constructed of one or more rigid materials to give the cartridge a primarily rigid construction. In another example, a removable cartridge is constructed of one or more flexible materials (e.g., a foil) to give the cartridge a primarily flexible construction. In one such example, pressure may be applied to the exterior of one or more reservoirs within cartridge 1005 to provide the force to move one or more consumer products therein out of the opening in passageway 1010 to a connector of an applicator device and onward to an applicator element.

FIG. 11 illustrates a cross sectional view of another exemplary implementation of a removable cartridge 1105 for holding one or more consumer products and attachment to an applicator device such as any of those described herein. Removable cartridge 1105 includes a main body portion and a passageway 1110 to an opening covered by removable cover 1115. In one example passageway 1110 is a cylindrical shape and cover 1115 is a screwable plug-like cover that can be removed by rotation from the opening at the top of passageway 1110. Passageway 1110 connects to reservoirs 1120 and 1125 within cartridge 1105. In one example, reservoirs 1120 and 1125 connect to passageway 1110. In one such example, passageway 1110 is a singular passageway in which consumer products from each of the two or more reservoirs pass to the opening in passageway 1110 to a connector of an applicator device (for delivery to an applicator element). In another such example, passageway 1110 includes a plurality of separated passageways, each connected to a different reservoir of reservoirs 1120 and 1125 within cartridge 1105, such that a consumer product from each reservoir can pass to the opening of passageway 1110 and to an applicator device without combining with others. In an alternative implementation (not shown), cartridge 1105 may include a mixing chamber configured to receive a consumer product from each of two or more reservoirs within cartridge 1105 prior to the combined mixture of consumer products being delivered to an applicator element of an applicator device via the opening in passageway 1110. A removable cartridge, such as cartridge 1105, cartridge 1005, cartridge 965, cartridge 865, etc., may be constructed of any of a variety of materials. In one example, a removable cartridge is constructed of one or more rigid materials to give the cartridge a primarily rigid construction. In another example, a removable cartridge is constructed of one or more flexible materials (e.g., a foil) to give the cartridge a primarily flexible construction. In one such example, pressure may be applied to the exterior of one or more reservoirs 1120, 1125 within cartridge 1105 to provide the force to move one or more consumer products therein out of the opening in passageway 1110 to a connector of an applicator device and onward to an applicator element.

FIG. 12 illustrates a cross sectional view of yet another exemplary implementation of a removable cartridge 1205 for holding one or more consumer products and attachment to an applicator device such as any of those described herein. Removable cartridge 1205 includes a main body portion and a passageway 1210 to an opening covered by removable cover 1215. In one example passageway 1210 is a cylindrical shape and cover 1215 is a screwable plug-like cover that can be removed by rotation from the opening at the top of passageway 1210. Passageway 1210 connects to reservoirs 1220, 1225, 1230 within cartridge 1205. In one example, reservoirs 1220 and 1225 connect to passageway 1210. In one such example, passageway 1210 is a singular passageway in which consumer products from each of the two or more reservoirs pass to the opening in passageway 1210 to a connector of an applicator device (for delivery to an applicator element). In another such example, passageway 1210 includes a plurality of separated passageways, each connected to a different reservoir of reservoirs 1220, 1225, 1230 within cartridge 1205, such that a consumer product from each reservoir can pass to the opening of passageway 1210 and to an applicator device without combining with others. In an alternative implementation (not shown), cartridge 1205 may include a mixing chamber configured to receive a consumer product from each of two or more reservoirs within cartridge 1205 prior to the combined mixture of consumer products being delivered to an applicator element of an applicator device via the opening in passageway 1210. A removable cartridge, such as cartridge 1205, cartridge 1005, cartridge 965, cartridge 865, etc., may be constructed of any of a variety of materials. In one example, a removable cartridge is constructed of one or more rigid materials to give the cartridge a primarily rigid construction. In another example, a removable cartridge is constructed of one or more flexible materials (e.g., a foil) to give the cartridge a primarily flexible construction. In one such example, pressure may be applied to the exterior of one or more reservoirs 1220, 1225, 1230 within cartridge 1205 to provide the force to move one or more consumer products therein out of the opening in passageway 1210 to a connector of an applicator device and onward to an applicator element.

FIG. 13 illustrates a cross sectional side perspective view of one exemplary implementation of a removable cartridge 1305 having one or more reservoirs for holding one or more consumer products and attachment to an applicator device such as any of those described herein. Removable cartridge 1305 is a flexible material (pouch-like) cartridge. Removable cartridge 1305 includes a main body portion and a passageway 1310 to an opening covered by removable cover 1315. In one example passageway 1310 is a cylindrical shape and cover 1315 is a screwable plug-like cover that can be removed by rotation from the opening at the top of passageway 1310. Passageway 1310 connects to one or more reservoirs within cartridge 1305. In one example, two or more reservoirs connect to passageway 1310. In one such example, passageway 1310 is a singular passageway in which consumer products from each of the two or more reservoirs pass to the opening in passageway 1310 to a connector of an applicator device (for delivery to an applicator element). In another such example, passageway 1310 includes a plurality of separated passageways, each connected to a different reservoir within cartridge 1305, such that a consumer product from each reservoir can pass to the opening of passageway 1310 and to an applicator device without combining with others. In an alternative implementation (not shown), cartridge 1305 may include a mixing chamber configured to receive a consumer product from each of two or more reservoirs within cartridge 1305 prior to the combined mixture of consumer products being delivered to an applicator element of an applicator device via the opening in passageway 1310. One or more consumer products may be delivered from one or more reservoirs of cartridge 1305 via a variety of mechanisms. In one example, a pumping element of a connected applicator device may pump one or more consumer products from cartridge 1305 via a connector (e.g., a conduit, a tube, etc.) that is placed in a corresponding reservoir of cartridge 1305. In another example, manual physical force (e.g., squeezing of cartridge 1305) may provide the force for delivering one or more consumer products from cartridge 1305 to a connected applicator device via the opening in passageway 1310.

FIG. 14 illustrates a cross sectional side perspective view of another exemplary implementation of a removable cartridge 1405 having one or more reservoirs for holding one or more consumer products and attachment to an applicator device such as any of those described herein. Removable cartridge 1405 is a flexible material (pouch-like) cartridge. Removable cartridge 1405 includes a main body portion and a passageway 1410 to an opening covered by removable cover 1415. In one example passageway 1410 is a cylindrical shape and cover 1415 is a screwable plug-like cover that can be removed by rotation from the opening at the top of passageway 1410. Passageway 1410 connects to one or more reservoirs within cartridge 1405. In one example, two or more reservoirs connect to passageway 1410. In one such example, passageway 1410 is a singular passageway in which consumer products from each of the two or more reservoirs pass to the opening in passageway 1410 to a connector of an applicator device (for delivery to an applicator element). In another such example, passageway 1410 includes a plurality of separated passageways, each connected to a different reservoir within cartridge 1405, such that a consumer product from each reservoir can pass to the opening of passageway 1410 and to an applicator device without combining with others. In an alternative implementation (not shown), cartridge 1405 may include a mixing chamber configured to receive a consumer product from each of two or more reservoirs within cartridge 1405 prior to the combined mixture of consumer products being delivered to an applicator element of an applicator device via the opening in passageway 1410. One or more consumer products may be delivered from one or more reservoirs of cartridge 1405 via a variety of mechanisms. In one example, a pumping element of a connected applicator device may pump one or more consumer products from cartridge 1405 via a connector (e.g., a conduit, a tube, etc.) that is placed in a corresponding reservoir of cartridge 1405. In another example, manual physical force (e.g., squeezing of cartridge 1405) may provide the force for delivering one or more consumer products from cartridge 1405 to a connected applicator device via the opening in passageway 1410. Removable cartridge 1405 is shown with a roller device 1420 that includes two rollers (e.g., connectably disposed on the outside of cartridge 1405) and configured to roll up cartridge 1405 to provide external pressure for forcing one or more consumer products out of the opening in passageway 1410 (e.g., when connected to an applicator device). In an alternative implementation, a single roller may be disposed adjacent cartridge 1405 for providing pressure to deliver one or more consumer products out of the opening in passageway 1410.

In another example implementation (not shown) of a consumer product cartridge for use in an applicator device, a deformable walled reservoir is included in a chamber of a cartridge. The deformable walled reservoir is configured (similar to other reservoirs discussed herein) to contain one or more consumer products. The chamber is configured to receive a pressure (e.g., a gas pressure from a pneumatic pumping element, a gas pressure from a manual mechanism, a mechanical pressure from a mechanical mechanism). The pressure exerts a force on the deformable walls of the reservoir forcing some and/or all of the consumer product from the reservoir to an applicator element (e.g., via one or more connectors).

Figure 15:
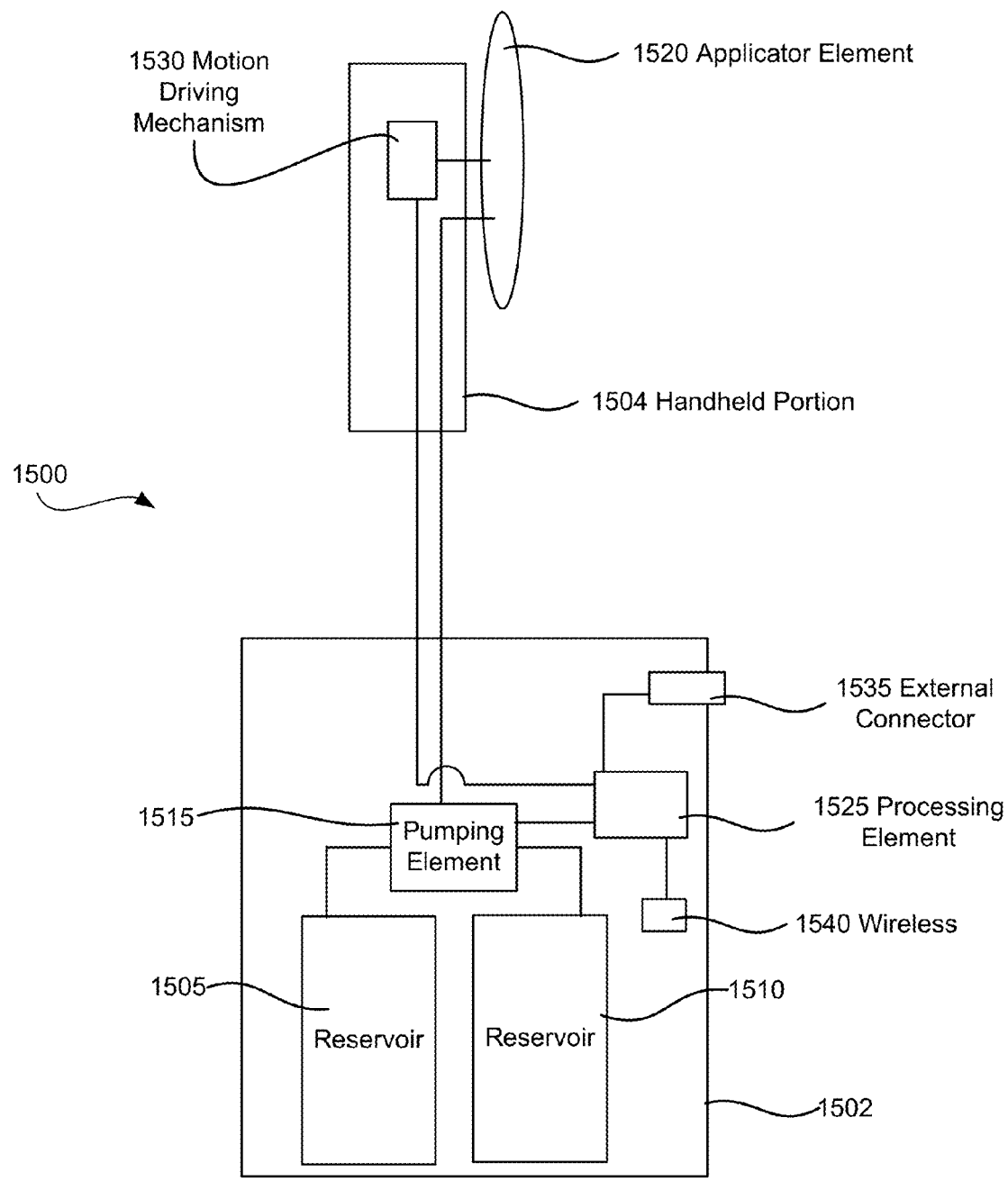
FIG. 15 illustrates an alternative embodiment of a device for application of one or more consumer products to a surface of a user.

FIG. 15 illustrates an alternative embodiment of a device 1500 for application of one or more consumer products to a surface of a user. For purposes of efficient disclosure, components of device 1500 that are similar to those of device 100 have similar features, aspects, functionalities, options, and alternatives as those discussed above with respect to device 100 (including the ability for optional components that are not shown in FIG. 1, but are discussed therein), except where described in a contrary fashion with respect to device 1500. Additional features, aspects, functionalities, options, and alternatives may be discussed with respect to a like component of device 1500, and are contemplated to be applicable (where not contrary to the discussion above) to the like components of device 100.

Device 1500 has a body 1502 and a separated hand-held portion 1504. Hand-held portion 1504 is flexibly connected to body 1502. In one example, body 1502 can be a larger (i.e., less portable) construction to which portion 1504 is connected such that portion 1504 can be manipulated by a user to bring an applicator element 1520 into contact with the surface to which one or more consumer products are to be applied.

Device 1500 includes a reservoir 1505 and a reservoir 1510 connected to a pumping element 1515 (e.g., via conduit), which is further connected (e.g., via conduit) to an applicator element 1520. Device 1500 also includes a processing element 1525 in electrical communication with pumping element 1515 for controlling the delivery of one or more consumer products from one or more of reservoirs 1505, 1510 to applicator element 1520. Device 1500 also includes a motion driving mechanism 1530 in electrical communication with processing element 1525 and including physical connection to application element 1520 for providing one or more motion features to application element 1520. Various motion features and components of a motion driving mechanism are discussed above. Motion driving mechanism 1530 is shown as part of portion 1504 with connection to processing element 1525 (e.g., via a flexible extension connector between body 1502 and portion 1504).

Device 1500 further includes an external connector 1535 in electrical communication with processing element 1525 for providing one or more connections to device 1500 to an external element via external connector 1535. In one such example, processing element 1525 may utilize information in a memory element to control the operation of external connector 1535, manage power input via external connector 1535 (e.g., to one or more components of device 1500 and/or to an internal power supply of device 1500), update information of a memory element using information from an external source via external connector 1535, manage a network connection, connect processing element 1525 to one or more user interfaces of a remote device and/or docking station/cradle, control the application of one or more consumer products from reservoirs 1505/410 (e.g., control dosing, control amounts of combinations of products and/or components thereof, control sequence of application of consumer products and/or components thereof, etc.) using information via external connector 1535 (e.g., information from a remote user device with user interface), and/or perform one or more other functions utilizing external connector 1535.

Device 1500 includes a wireless communication functionality 1540 in electrical communication with processing element 1525. Exemplary functionalities for a wireless communication functionality are discussed above. In one example, device 1500 may also include as part of body 1502 more comprehensive user interface controls (e.g., buttons, displays, etc.) than may be on a more portable embodiment.

Figure 16:
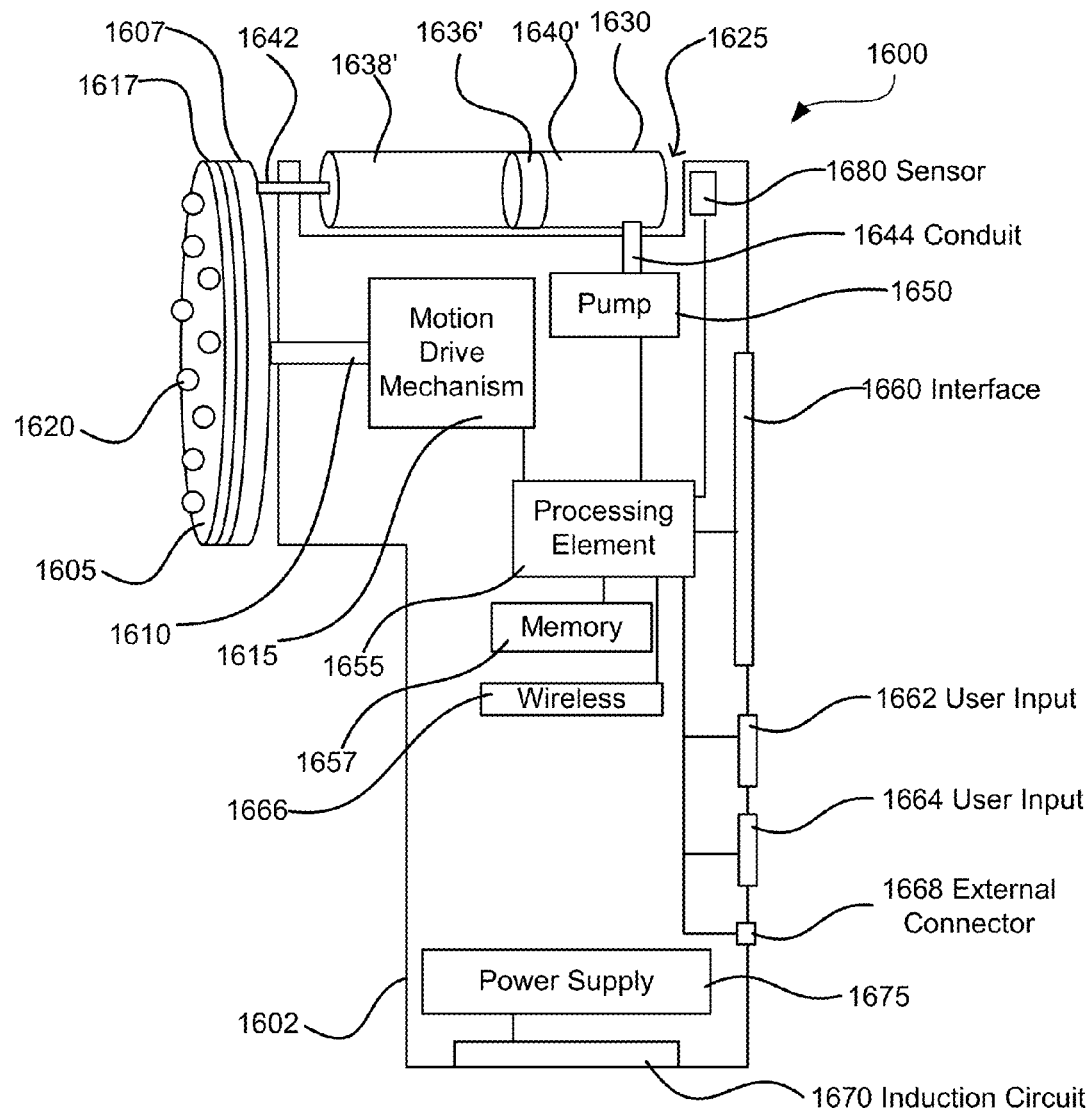
FIG. 16A illustrates a cross sectional view of still yet another exemplary implementation of a device for application of one or more consumer products to a surface of a user.
FIG. 16B illustrates a top-down cross sectional view of one exemplary implementation of a consumer products cartridge.
Figure 16:
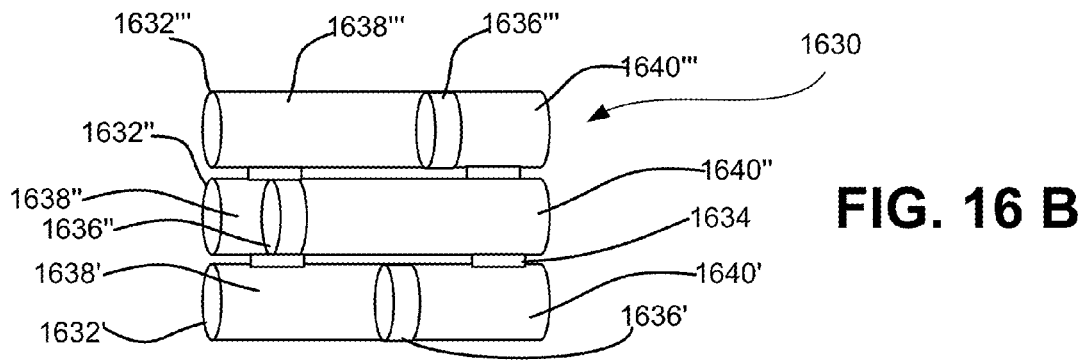

FIG. 16A illustrates a cross sectional view of still yet another exemplary implementation of a device 1600 for application of one or more consumer products to a surface of a user. For purposes of efficient disclosure, components of device 1600 that are similar to those of other devices discussed herein may have similar features, aspects, functionalities, options, and alternatives as those discussed above with respect to those devices, except where described in a contrary fashion with respect to device 1600. Additional features, aspects, functionalities, options, and alternatives may be discussed with respect to a like component of device 400, and are contemplated to be applicable (where not contrary to the discussion above) to the like components of device 100, 200, 300, 400, 500, 600, 800, 900, and/or 1500.

Device 1600, having a device body 1602, includes an applicator element 1605 configured for applying one or more consumer products to a surface of a subject and/or to work the one or more consumer products onto the surface of the subject. Applicator element 1605 includes a structural disc component 1607 attached to a structural connection element 1610. Structural connection element 1610 is connected to a motion drive mechanism 1615 that is configured to drive one or more motion features of applicator element 1605. Applicator element 1605 also includes a removable component 1617, having a textured surface 1620. Removable component 1617 is shown in an installed position on structural disc component 1607. Ways for attaching a removable portion of an applicator element are discussed above.

Device 1600 also includes a receptacle 1625 configured to receive and hold a consumer product cartridge 1630. Consumer product cartridge 1630 is illustrated with a top side, cross-sectional view in FIG. 16B. In this example, consumer product cartridge 1630 includes three sub-cartridges 1632', 1632", and 1632''' that are connected together with cartridge connections 1634 (four such connections shown in FIG. 16A). In an alternative implementation, each of sub-cartridges 1632', 1632", and 1632''' can be a separate cartridge that can be inserted into a properly configured portion of receptacle 1625 and/or separate receptacles of device 1600. Any number of sub-cartridges may be included in alternative examples. Each of sub-cartridges 1632', 1632", and 1632''' includes a piston 1636', 1636", 1636''', respectively, moveably positioned inside each sub-cartridge separating the sub-cartridge into two compartments: consumer product reservoirs 1638', 1638", and 1638''' on one side, respectively, and air chambers 1640', 1640", and 1640''' on the other, respectively. Pistons 1636', 1636", 1636''' are each shown in different positions to illustrate the ability of the pistons to move to provide pressure on a consumer product in a corresponding reservoir to force the consumer product out via a conduit or directly onto, an applicator element. The operation of the pistons in device 1600 is described in more detail below.

In FIG. 16A, cartridge 1630 is shown inserted into receptacle 1625 with one sub-cartridge 1632' illustrated in a side cross-sectional view showing piston 1636', air chamber 1640', and reservoir 1638'. When inserted into receptacle 1625, an opening in each of reservoirs 1638', 1638", and 1638''' is connected with connector 1642, which is positioned and configured to receive consumer product from each reservoir and deliver the consumer product to applicator disc 1605. Many variations of configurations of connector 1642 will be apparent from the current disclosure. In one example, connector 1642 includes a branched conduit that connects to each reservoir with a separate connection and includes a single output conduit in functional positioning with a surface of applicator element 1605. In another example, connector 1642 includes separate conduit connections to each reservoir with corresponding separate output connections with a surface of applicator element 1605. Cartridge 1630 may include a pre-configured opening in its body for each of its reservoirs for connection to connector 1642. In one example, such one or more openings may include one or more corresponding covers that enclose each reservoir when the cartridge is not inserted. Example covers for a reservoir include, but are not limited to, a foil seal, a screw-attachment cover, a snap-attachment cover, and any combinations thereof. A cover may provide protection from the elements (such as air, light, etc.) to the consumer product in a cartridge. Such a cover may be pierced by connector 1642 and/or another component of device 1600. In another example, such a cover may be removed by a user prior to installation of cartridge 1630. Applicator element 1605 includes at least one structural element for accepting one or more consumer products from connector 1642 and providing the consumer product to surface 1620 for application to a user. Examples of such a structural element include, but are not limited to, a porous component of applicator element 1605 that receives a consumer product from connector 1642 and allows it to pass (e.g., from pressure provided by pumping element 1650 and corresponding piston 1636) to surface 1620, a removable component 1617 constructed of a porous material that allows a consumer product from connector 1642 to pass to surface 1620, a passageway in one or more components of applicator element 1605 that provide a conduit from the connector 1642 to surface 1620 and allow a consumer product to pass through to surface 1620 (e.g., under pressure from pumping element 1650), and any combinations thereof. In an alternative implementation, connector 1642 may be configured to terminate at surface 1620 directly (e.g., by positioning around applicator element 1605 such that an opening in connector 1642 is in contact or near contact with surface 1620).

Also, when inserted into receptacle 1625, an opening in each of air chambers 1640', 1640", and 1640''' is connected with conduit 1644, which is positioned and configured to provide connection between each air chamber and a pumping element 1650. Many variations of configurations for conduit 1644 may be employed. In one example, conduit 1644 includes a branched conduit that connects to each reservoir with a separate connection and includes a single input conduit in functional connection with pumping element 1650. In another example, conduit 1644 includes separate conduit connections to each air chamber with separate conduit connections to pumping element 1650. Pumping element 1650 may control each air chamber individually. In another example pumping element 1650 may control any two or more air chambers with the same input pressure. A cover may be provided over each opening in an air chamber. Example covers are discussed above.

Device 1600 includes a processing element 1655. Processing element may include a memory and/or have an optional additional memory element 1657. Additional optional elements are shown in FIG. 16A: a user interface 1660, a user input 1662, a user input 1664, a wireless communications functionality 1666, an external connector 1668, and an induction power coupling circuitry 1670. The induction power coupling circuitry could be utilized in one or more examples to provide an input of electrical power to a power supply 1675. In other examples, power supply 1675 may obtain power from alternative connections and/or have a removable power component. Power supply 1675 provides power to one or more of the components via electrical connections to such components (not shown). Processing element 1655 is connected to various components of device 1600 to provide control of such components. For example, processing element 1655 controls pumping element 1650 to provide air pressure selectively to air chambers 1640', 1640", 1640''', respectively. This air pressure drives one or more pistons 1636', 1636", 1636''' to pressure a corresponding consumer product in reservoir 1638', 1638", 1638''', respectively, to be delivered via connector 1642 to a surface of applicator element 1605.

Device 1600 also includes a consumer product sensor 1680. Sensor 1680 may include one or more sensor components for detecting information from one or more cartridges (and/or sub-cartridges) in receptacle 1625. Example sensor components include, but are not limited to, an information reader component (e.g., a component configured to read an identification element of a cartridge and/or subcartridge), an optical sensor (e.g., an optical sensor configured to detect a position of one or more pistons in a cartridge and/or subcartridge), a sensor for detecting the amount of consumer product in a reservoir, and any combinations thereof. In one example, sensor 1680 includes electrical components (e.g., an light detector element/sensor) positioned to provide a sensing beam of light into a cartridge and/or subcartridge to detect a position of a surface within the cartridge and/or subcartridge (e.g., a surface of a consumer product therein, a surface of a piston therein, etc.). The position information can then be utilized by processing element 1655 to determine, for example, how much of a consumer product remains in a reservoir, how fast a consumer product is being dispensed from a reservoir, and/or one or more other operational aspects of the dispensing process.

Figure 17:
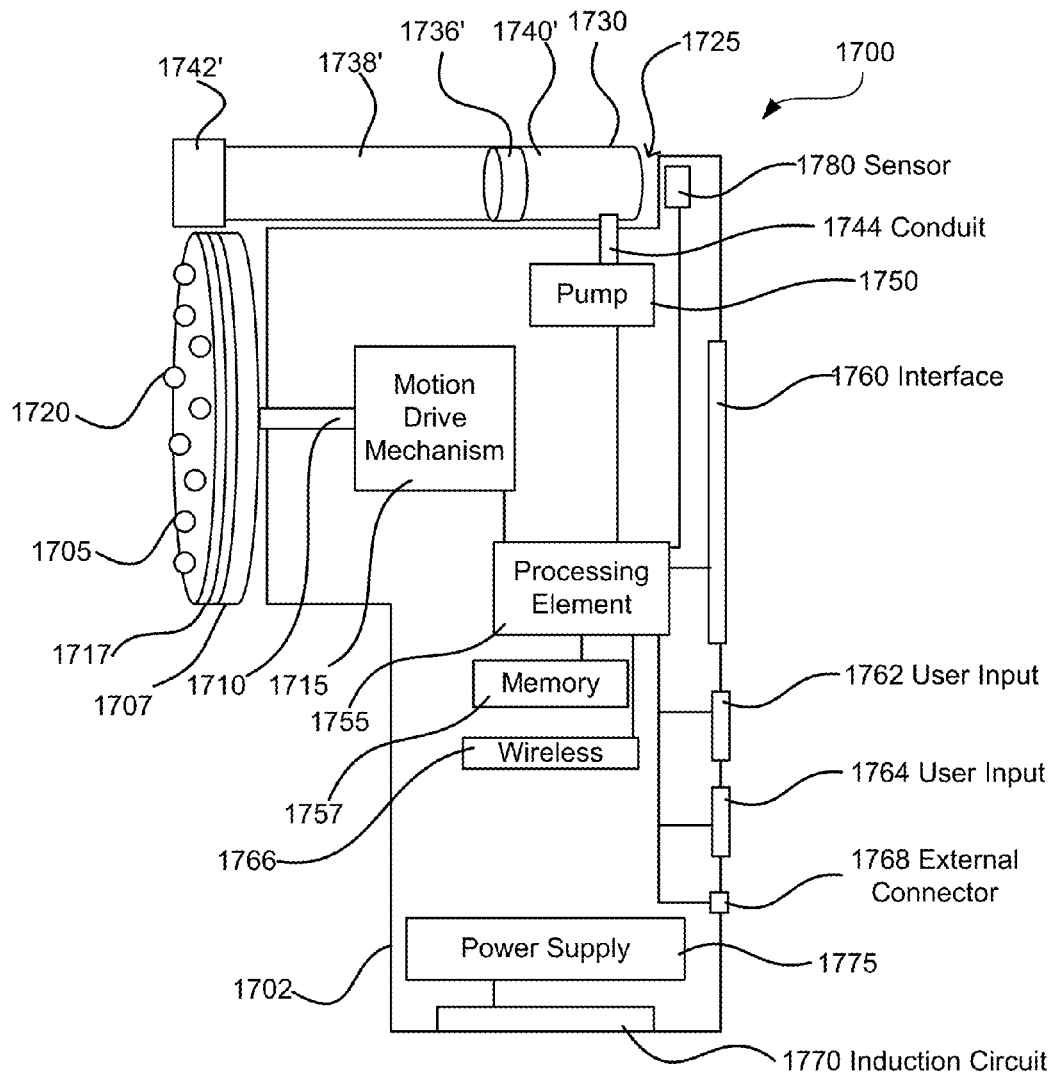
FIG. 17A illustrates a cross sectional view of a further exemplary implementation of a device for application of one or more consumer products to a surface of a user.
FIG. 17B illustrates a top-down cross sectional view of another exemplary implementation of a consumer products cartridge.
Figure 17:
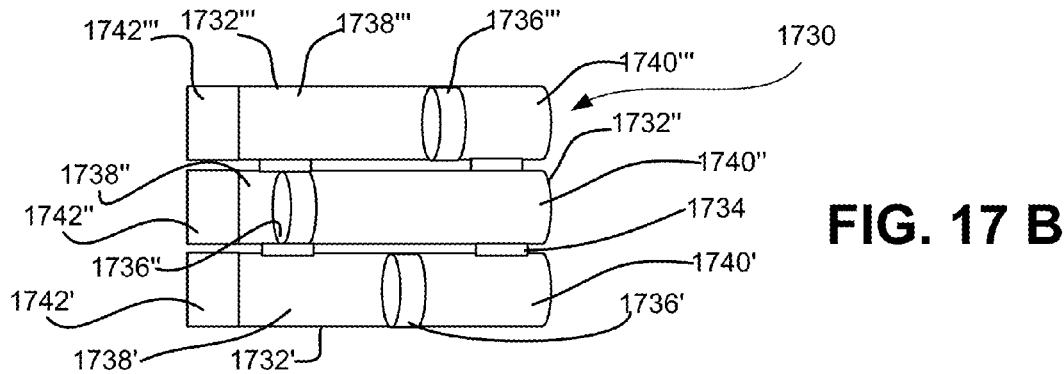

FIG. 17A illustrates a cross sectional view of still yet another exemplary implementation of a device 1700 for application of one or more consumer products to a surface of a user. For purposes of efficient disclosure, components of device 1700 that are similar to those of other devices discussed herein may have similar features, aspects, functionalities, options, and alternatives as those discussed above with respect to those devices, except where described in a contrary fashion with respect to device 1700. Additional features, aspects, functionalities, options, and alternatives may be discussed with respect to a like component of device 400, and are contemplated to be applicable (where not contrary to the discussion above) to the like components of device 100, 200, 300, 400, 500, 600, 800, 900, and/or 1500.

Device 1700, having a device body 1702, includes an applicator element 1705 configured for applying one or more consumer products to a surface of a subject and/or to work the one or more consumer products onto the surface of the subject. Applicator element 1705 includes a structural disc component 1707 attached to a structural connection element 1710. Structural connection element 1710 is connected to a motion drive mechanism 1715 that is configured to drive one or more motion features of applicator element 1705. Applicator element 1705 also includes a removable component 1717, having a textured surface 1720. Removable component 1717 is shown in an installed position on structural disc component 1707. Ways for attaching a removable portion of an applicator element are discussed above. In device 1700, applicator element 1705 is designed to be utilized in combination with a second applicator element component 1742 (shown as three sub-components 1742', 1742", and 1742'" and discussed further below).

Device 1700 also includes a receptacle 1725 configured to receive and hold a consumer product cartridge 1730. Consumer product cartridge 1730 is illustrated with a top side, cross-sectional view in FIG. 17B. In this example, consumer product cartridge 1730 includes three sub-cartridges 1732', 1732", and 1732'" that are connected together with cartridge connections 1734 (four such connections shown in FIG. 17A). In an alternative implementation, each of sub-cartridges 1732', 1732", and 1732'" can be a separate cartridge that can be inserted into a properly configured portion of receptacle 1725 and/or separate receptacles of device 1700. Any number of sub-cartridges can exist in other alternative examples. Each of sub-cartridges 1732', 1732", and 1732'" includes a piston 1736', 1736", 1736'", respectively, moveably positioned inside each sub-cartridge separating the sub-cartridge into two compartments: consumer product reservoirs 1738', 1738", and 1738'" on one side, respectively, and air chambers 1740', 1740", and 1740'" on the other, respectively. Pistons 1736', 1736", 1736'" are each shown in different positions to illustrate the ability of the pistons to move to provide pressure on a consumer product in a corresponding reservoir to force the consumer product out via a conduit or directly onto, an applicator element. The operation of the pistons in device 1700 is described in more detail below. Each sub-cartridge 1732', 1732", and 1732'" includes a portion of an applicator element 1742 (1742', 1742", 1742'", respectively). Each applicator element sub-component 1742', 1742", 1742'" is connected to a corresponding reservoir 1738', 1738", 1738'". In one example, each applicator element sub-component 1742', 1742", 1742'" includes a porous material (e.g., a porous foam, a porous plastic) that is configured to allow a consumer product from within the corresponding reservoir 1738', 1738", 1738'" to pass to an outer surface of sub-component 1742', 1742", 1742'" to allow the consumer product to be applied to the surface of a subject. In other examples, each of sub-component 1742', 1742", 1742'" may include any material capable of allowing passage of a particular consumer product to one or more of its outer surfaces. In one such example, the material of each sub-component 1742', 1742", 1742'" is chosen based on a physical and/or chemical property of the corresponding consumer product to be contained in reservoir 1738', 1738", 1738'", respectively. In yet another example, one or more of sub-component 1742', 1742", 1742'" includes a connector (not shown, such as a conduit or other passageway) to allow a consumer product to pass from a corresponding reservoir to a surface of the applicator element sub-component. Any combinations of these examples may exist in a single cartridge with multiple sub-cartridges. Applicator element 1705 can be used to work one or more consumer products into a surface of a subject after initial application.

In FIG. 17A, cartridge 1730 is shown inserted into receptacle 1725 with one sub-cartridge 1732' illustrated in a side cross-sectional view showing piston 1736', air chamber 1740', and reservoir 1738'. When inserted into receptacle 1725, each of applicator element sub-components 1742', 1742", 1742'" is positioned adjacent applicator element 1705 to allow for contact with a surface of a subject. A cover may be provided over one or more surfaces of applicator element sub-components 1742', 1742", 1742'" to protect the contents of corresponding reservoirs. Example covers include, but are not limited to, a foil seal, a screw-attachment cover, a snap-attachment cover, and any combinations thereof. A cover may provide protection from the elements (such as air, light, etc.) to the consumer product in a cartridge. In one example, such a cover may be removed by a user prior to use. In another example, such a cover may be water soluble and dissolved with water at time of use.

Any one or more of applicator element sub-components 1742', 1742", 1742'" may be removable from cartridge 1730. In one exemplary aspect, such removability may allow for replacement of worn, damaged, and/or contaminated applicator element sub-components. Example connections for a removable applicator element sub-component may be similar to removable connections for applicator elements discussed above. In one example, an applicator element sub-component is attached to a reservoir, cartridge, and/or sub-cartridge with a screw-type connection. In another example, an applicator element sub-component is attached to a reservoir, cartridge, and/or sub-cartridge with a snap-type connection. In yet another example, an applicator element sub-component is attached to a reservoir, cartridge, and/or sub-cartridge with a pressure fit connection.

It is noted that the aspects, features, and functionalities of applicator elements similar to applicator element 1742 (and its sub-components) can be applied to one or more reservoirs that are not removable from a device (e.g., are not associated with a removable cartridge).

Also, when inserted into receptacle 1725, an opening in each of air chambers 1740', 1740", and 1740''' is connected with conduit 1744, which is positioned and configured to provide connection between each air chamber and a pumping element 1750. Many variations of configurations for conduit 1744 may be employed. In one example, conduit 1744 includes a branched conduit that connects to each reservoir with a separate connection and includes a single input conduit in functional connection with pumping element 1750. In another example, conduit 1744 includes separate conduit connections to each air chamber with separate conduit connections to pumping element 1750. Pumping element 1750 may control each air chamber individually. In another example pumping element 1750 may control any two or more air chambers with the same input pressure. A cover may be provided over each opening in an air chamber. Example covers are discussed above.

Device 1700 includes a processing element 1755. Processing element may include a memory and/or have an optional additional memory element 1757. Additional optional elements are shown in FIG. 17A: a user interface 1760, a user input 1762, a user input 1764, a wireless communications functionality 1766, an external connector 1768, and an induction power coupling circuitry 1770. The induction power coupling circuitry could be utilized in one or more examples to provide an input of electrical power to a power supply 1775. In other examples, power supply 1775 may obtain power from alternative connections and/or have a removable power component. Power supply 1775 provides power to one or more of the components via electrical connections to such components (not shown). Processing element 1755 is connected to various components of device 1700 to provide control of such components. For example, processing element 1755 controls pumping element 1750 to provide air pressure selectively to air chambers 1740', 1740", 1740''', respectively. This air pressure drives one or more pistons 1736', 1736", 1736''' to pressure a corresponding consumer product in reservoir 1738', 1738", 1738''', respectively, to be delivered to a surface of a corresponding applicator element sub-component 1742', 1742", 1742'''. While applicator element sub-components 1742', 1742", 1742''' are referred to as sub-components, it is contemplated that each may also be referred to as simply an applicator element. A device according to the current disclosure may have any number of applicator elements as is necessary for a particular implementation design.

Device 1700 also includes a consumer product sensor 1780. Sensor 1780 may include one or more sensor components for detecting information from one or more cartridges (and/or sub-cartridges) in receptacle 1725. Example sensor components include, but are not limited to, an information reader component (e.g., a component configured to read an identification element of a cartridge and/or subcartridge), an optical sensor (e.g., an optical sensor configured to detect a position of one or more pistons in a cartridge and/or subcartridge), a sensor for detecting the amount of consumer product in a reservoir, and any combinations thereof. In one example, sensor 1780 includes electrical components (e.g., an light detector element/sensor) positioned to provide a sensing beam of light into a cartridge and/or subcartridge to detect a position of a surface within the cartridge and/or subcartridge (e.g., a surface of a consumer product therein, a surface of a piston therein, etc.). The position information can then be utilized by processing element 1755 to determine, for example, how much of a consumer product remains in a reservoir, how fast a consumer product is being dispensed from a reservoir, and/or one or more other operational aspects of the dispensing process.

It is noted that any of the embodiments and implementations above can be implemented with a single reservoir system. For example, an applicator device may include a single reservoir for holding one or more consumer products. Such an applicator device may include any combination or subcombination of components discussed above with respect to the various applicator device embodiments (e.g., device 100, 200, 300, 400, 500, 600, 800, 900, 1500, 1600) such that are consistent with a single reservoir system, such as a pumping element, a manual force setup, a processing element, an external connector, a wireless communication functionality, a power supply, an identification element, an identification reader mechanism, a removable cartridge, connection to a remote device, control and/or user interface via a remote device, connection to a docking station/cradle, a motion driving mechanism, a motor, motion connection configurations, and any combinations thereof.

It is also noted that a reservoir as described herein (e.g., a reservoir in a cartridge) and/or a different chamber may include water (e.g., an ionized water, a mineralized water, etc.) for application alone, in combination with another consumer product, and/or in sequence with another consumer product. An applicator device may include (e.g., as part of a pumping element), a pressurizing component that is configured to pressurize the water (or another consumer product) before application via an applicator element. Such pressurization may allow water to be jetted from an opening in an applicator element. Water may also be applied as a mist. Water may be cooled and/or heated (e.g., using a cooling element or a heating element of an applicator device) prior to application. In one example, a reservoir or alternate chamber of a device include a piezoelectric element that is configured to excite water contained in the reservoir/chamber to form a mist and/or a vapor prior to application to a subject.

Various methods of applying one or more consumer products using an applicator device of the present disclosure will be clear from the discussions herein. For example, a user of an applicator device may insert a cartridge into a portable applicator device. The cartridge may include a plurality of reservoirs that are connected to a pumping element upon attachment of the cartridge to the applicator device. The pumping element delivers a first consumer product from a first reservoir to an applicator element of the applicator device for application to a skin (or other surface) of the user. After a set duration of application, the pumping element delivers a second consumer product from a second reservoir to the applicator element for application to the skin. The pumping element and the motion of the applicator element are controlled by a processing element for duration of application, dosage/amount of product applied, type of motion, etc. The user gets a visual indication of information regarding the application (including time/date of application, instance of application in a schedule/regimen, dosage/amount of application, sequence information for application, historical information regarding previous applications in the sequence, etc.) via a display of an app on their smartphone that is connected to the applicator device via a Bluetooth connection. Other variations on the method are apparent in light of the full disclosure herein.

Examples of other variations of dispensing one or more consumer products from a plurality of reservoirs to a surface of a subject via an application element of a device of this disclosure include dispensing one consumer product in a given application event, dispensing two or more consumer products in series in a given application event, dispensing two or more consumer products in combination in a given application event, and any combinations thereof. In one example, a first consumer product is delivered to an applicator element of a device from a first reservoir, the first consumer product is applied to a subject surface, a second consumer product is delivered to an applicator element of the device from a second reservoir, the second consumer product is applied to a subject surface, and (optionally) a motion is applied to an applicator element of the device in contact with the subject surface. In another example, a first portion of a first consumer product is delivered to an applicator element of a device from a first reservoir, the first portion of the first consumer product is applied to a subject surface, a first portion of a second consumer product is delivered to an applicator element of a device from a second reservoir, the first portion of the second consumer product is applied to a subject surface, a second portion of the first consumer product is delivered to an applicator element of the device from the first reservoir, the second portion is applied to a subject surface, and (optionally) a motion is applied to an applicator element of the device in contact with the subject surface. Alternation as in the previous example may occur in any combinations for any number of consumer products in any number of reservoirs. A processing element (e.g., with appropriate instructions and/or data stored in a memory) may control the timing of application (e.g., with or without motion) of one or more consumer products (e.g., individual timing and/or combined timing of multiple consumer products), indications/alerts to a user regarding timing of application of any one or more consumer products, timing between applications, indications/alerts to a user regarding timing between applications (e.g., start/stop signals from a output device), alternations of consumer products, combinations of consumer products, reminders to users to start an application regimen, other features and functions of applications. Data regarding applications (e.g., timing, date, dosage, conformity with prescribed/recommended routines from a service provider, other information) may be stored for later access by the user or a user of a remote device connected to the applicator device.

One exemplary potential benefit of a device and/or method of the current disclosure is the protection of a consumer product from exposure to environmental factors until the time of actual application to the surface of a subject. A device of the current disclosure can be configured to have connections to a reservoir that are sealed from the outside environment once a consumer product is added to the reservoir. Example ways for sealing from the outside environment include, but are not limited to, sealing a connection between a reservoir and a connector of the device, sealing a connection between a reservoir and an applicator element of a device, sealing a connection between a reservoir and a component of a pumping element of a device, using a cover over an opening in a reservoir, use of gaskets and other sealing mechanisms, providing a cartridge with air-tight seals between the connections of the cartridge to components of a device, having a piston with minimal air travel past the piston to an adjacent reservoir chamber, using pressure on a reservoir to keep external air outside and/or minimized to exposure of the consumer product only at the opening towards the adjacent applicator element, minimizing the size of openings in a reservoir, use of materials for reservoir walls that are non-light-transparent, and any combinations thereof. In one example, a cartridge with multiple reservoirs includes covers over any openings that are configured to be removed just prior to connection to a device of the current disclosure, the device having sealing mechanisms to minimize air transfer into the reservoirs once connected. Other examples of these concepts are discussed throughout the different examples of devices and cartridges above and various combinations of features will be apparent from the discussion herein.

It is to be noted that the aspects and embodiments described herein may be conveniently implemented using one or more machines (e.g., one or more computing devices/computer systems that are part of an aquatic environment monitoring and/or dosing system) including hardware and special programming according to the teachings of the present specification, as will be apparent to those of ordinary skill in the computer art. Appropriate software coding can readily be prepared by skilled programmers based on the teachings of the present disclosure, as will be apparent to those of ordinary skill in the software art.

Such software may be a computer program product that employs a machine-readable hardware storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable hardware storage medium include, but are not limited to, a magnetic disk (e.g., a conventional floppy disk, a hard drive disk), an optical disk (e.g., a compact disk "CD", such as a readable, writeable, and/or rewritable CD; a digital video disk "DVD", such as a readable, writeable, and/or rewritable DVD), a magneto-optical disk, a read-only memory "ROM" device, a random access memory "RAM" device, a magnetic card, an optical card, a solid-state memory device (e.g., a flash memory), an EPROM, an EEPROM, and any combinations thereof. A machine-readable storage medium, as used herein, is intended to include a single medium as well as a collection of physically separate media, such as, for example, a collection of compact disks or one or more hard disk drives in combination with a computer memory. As used herein, a machine-readable storage medium does not include a signal. A machine-readable storage medium may be included as part of a memory element in an applicator device as disclosed herein.

Such software may also include information (e.g., data) carried as a data signal on a data carrier, such as a carrier wave. Such a data signal or carrier wave would not be considered a machine-readable hardware storage medium. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device (e.g., a remote device for connection to an applicator device) include, but are not limited to, a computer workstation, a terminal computer, a server computer, a handheld device (e.g., tablet computer, a personal digital assistant "PDA", a mobile telephone, etc.), a web appliance, a network router, a network switch, a network bridge, any machine capable of executing a sequence of instructions that specify an action to be taken by that machine, and any combinations thereof. In one example, a computing device may include and/or be included in, a kiosk. In another example, a dosing calculator (as discussed herein) may be associated with (e.g., be part of, be connected to, be included in, etc.) a computing device or any part thereof. It is noted that aspects of an applicator device may include components of a computing device (such as a processing element and a memory for executing machine-executable instructions for operating one or more components of the applicator device. A person of ordinary skill will understand any of the components of the exemplary computing system 1600 discussed below that are needed for implementation of one or more of the functionalities of a component of an applicator device of the present disclosure are contemplated to be includable in an implementation thereof.

Figure 18:
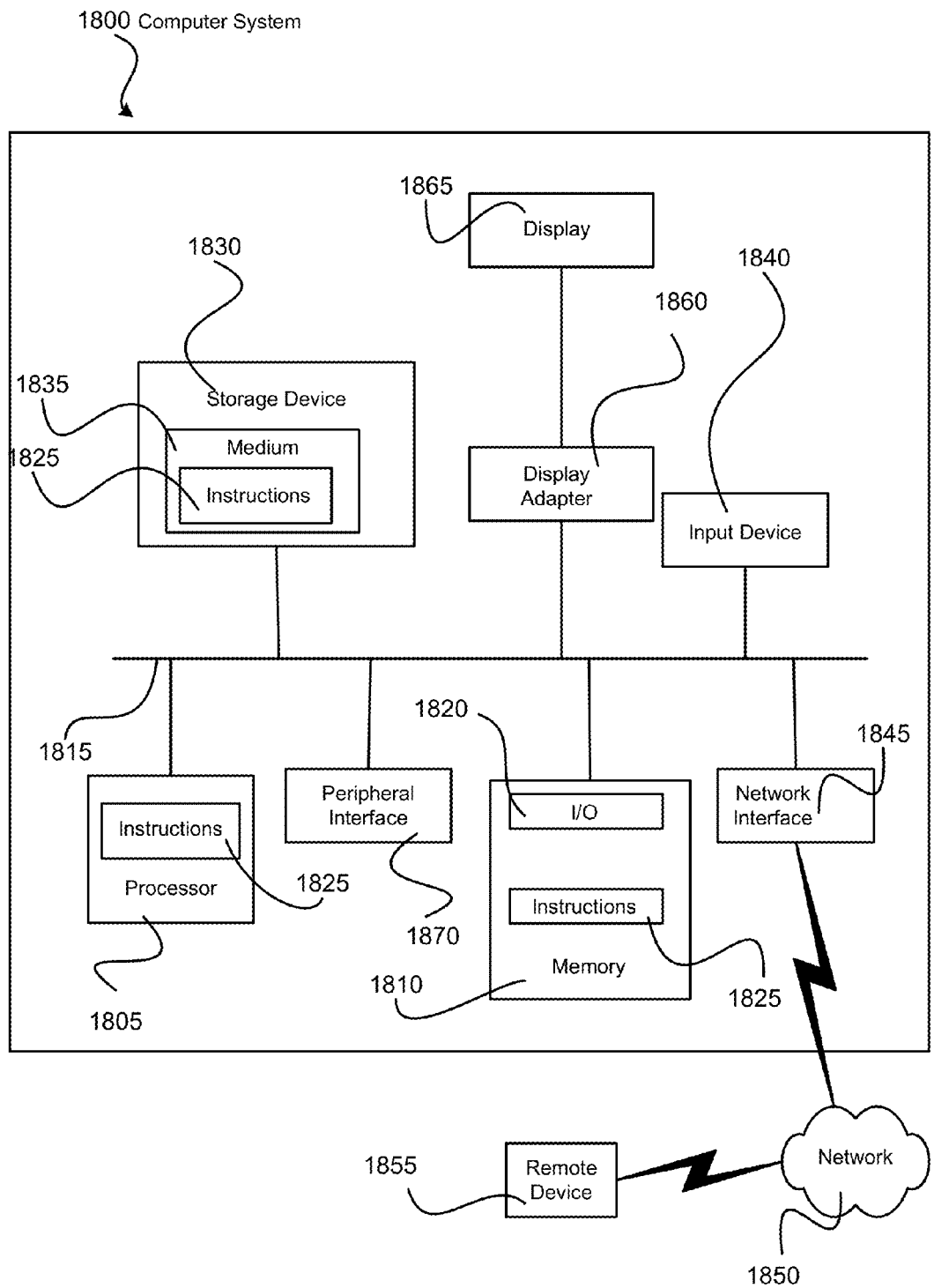
FIG. 18 illustrates one exemplary implementation of a computing device environment.

FIG. 18 shows a diagrammatic representation of one exemplary embodiment of a computing system 1800, within which a set of instructions for causing one or more processors 1804 to perform any one or more of the functionalities, aspects, and/or methodologies of the present disclosure. It is also contemplated that multiple computing systems may be utilized to implement a specially configured set of instructions for performing any one or more of the functionalities, aspects, and/or methodologies of the present disclosure in a distributed computing matter.

Computing system 1800 can also include a memory 1808 that communicates with the one or more processors 1804, and with other components, for example, via a bus 1812. Bus 1812 may include any of several types of bus structures including, but not limited to, a memory bus, a memory controller, a peripheral bus, a local bus, and any combinations thereof, using any of a variety of bus architectures.

Memory 1808 may include various components (e.g., machine-readable hardware storage media) including, but not limited to, a random access memory component (e.g., a static RAM "SRAM", a dynamic RAM "DRAM", etc.), a read only component, and any combinations thereof. In one example, a basic input/output system 1816 (BIOS), including basic routines that help to transfer information between elements within computing system 1800, such as during start-up, may be stored in memory 1808. Memory 1808 may also include (e.g., stored on one or more machine-readable hardware storage media) instructions (e.g., software) 1820 embodying any one or more of the aspects and/or methodologies of the present disclosure. In another example, memory 1808 may further include any number of program modules including, but not limited to, an operating system, one or more application programs, other program modules, program data, and any combinations thereof.

Computing system 1800 may also include a storage device 1824, such as, but not limited to, the machine readable hardware storage medium described above. Storage device 1824 may be connected to bus 1812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1824 (or one or more components thereof) may be removably interfaced with computing system 1800 (e.g., via an external port connector (not shown)). Particularly, storage device 1824 and an associated machine-readable medium 1828 may provide nonvolatile and/or volatile storage of machine-readable instructions, data structures, program modules, and/or other data for computing system 1800. In one example, software instructions 1820 may reside, completely or partially, within machine-readable hardware storage medium 1828. In another example, software instructions 1820 may reside, completely or partially, within processors 1804.

Computing system 1800 may also include an input device 1832. In one example, a user of computing system 1800 may enter commands and/or other information into computing system 1800 via one or more input devices 1832. Examples of an input device 1832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touch screen, and any combinations thereof. Input device(s) 1832 may be interfaced to bus 1812 via any of a variety of interfaces (not shown) including, but not limited to, a serial interface, a parallel interface, a game port, a USB interface, a FIREWIRE interface, a direct interface to bus 1812, and any combinations thereof. Input device(s) 1832 may include a touch screen interface that may be a part of or separate from display(s) 1836, discussed further below. Input device(s) 1832 may be utilized as a user selection device for selecting one or more graphical representations in a graphical interface as described above.

A user may also input commands and/or other information to computing system 1800 via storage device 1824 (e.g., a removable disk drive, a flash drive, etc.) and/or network interface device(s) 1840. A network interface device, such as any one of network interface device(s) 1840 may be utilized for connecting computing system 1800 to one or more of a variety of networks, such as network 1844, and one or more remote devices 1848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network, a telephone network, a data network associated with a telephone/voice provider, a direct connection between two computing devices, and any combinations thereof. A network, such as network 1844, may employ a wired and/or a wireless mode of communication. In general, any network topology may be used. Information (e.g., data, software instructions 1820, etc.) may be communicated to and/or from computing system 1800 via network interface device(s) 1840.

Computing system 1800 may further include one or more video display adapter 1852 for communicating a displayable image to one or more display devices, such as display device(s) 1836. Examples of a display device include, but are not limited to, a liquid crystal display (LCD), a cathode ray tube (CRT), a plasma display, a light emitting diode (LED) display, a virtual reality (VR) display device, and any combinations thereof. Display adapter(s) 1852 and display device(s) 1836 may be utilized in combination with processor(s) 1804 to provide a graphical representation of a utility resource, a location of a land parcel, and/or a location of an easement to a user. In addition to a display device, computing system 1800 may include one or more other peripheral output devices including, but not limited to, an audio speaker, a printer, and any combinations thereof. Such peripheral output devices may be connected to bus 1812 via a peripheral interface 1856. Examples of a peripheral interface include, but are not limited to, a serial port, a USB connection, a FIREWIRE connection, a parallel connection, and any combinations thereof.

In one example, a device for application of consumer products to an outer surface of a mammalian subject is provided. The device includes a plurality of reservoirs, each of the plurality of reservoirs for holding a consumer product; an applicator element configured to apply one or more of the consumer products to an outer surface of a subject; a pumping element connected via one or more channel elements to the plurality of reservoirs and the applicator element, the pumping element configured to deliver one or more of the consumer products to a first surface of the applicator element; a processing element for controlling the pumping element to selectively deliver a first consumer product from a first one of the plurality of reservoirs to the applicator element in series and/or in combination with a second consumer product from a second one of the plurality of reservoirs. In one such example, at least one of the plurality of reservoirs is a cartridge removeable from the device. In another such example, the cartridge includes at least two of the plurality of reservoirs. In yet another such example, the cartridge is disposable. The cartridge may include an identification element. The cartridge may include an identification element and the device further includes a reading element in communication with the processing element and configured to read one or more data from the identification element when the cartridge is inserted to the device. One or more data may include a data selected from the group consisting of an identification of a consumer product within the cartridge, a sequence order for administering a plurality of consumer product, an expiration date of a consumer product within the cartridge, a prescription for a consumer fluid within the cartridge, an instruction for application of a consumer product within the cartridge, a dosing instruction for a consumer product within the cartridge, and any combinations thereof. The pumping element may include one or more micro-pumps. The processing element may include a microprocessor. In another such example, the processing element may include one or more static programmed circuit elements. The device in this example may further include one or more external port connectors in communication with the processing element. The one or more external port connectors may include a port selected from the group consisting of a power connection, a data connection, a network connection, and any combinations thereof. The device of this example may include a wireless network functionality. The wireless network functionality may include a functionality selected from the group consisting of a wi-fi functionality, a Bluetooth functionality, a radio frequency functionality, an optical networking functionality, and any combinations thereof. The device of this example may include a network connection. The network connection may connect to a remote location selected from the group consisting of a pharmacy, a manufacturer of the device, a supplier of the device, a service provider associated with one or more of the consumer fluids, a service provider associated with the device, a user computing device, and any combinations thereof. A user computing device may include a device selected from the group consisting of a smartphone, a PDA, a mobile computer, a handheld computer, a laptop computer, a tablet, a desktop computer, a network computer, a kiosk, and any combinations thereof. The device of this example may include a display in communication with the processing element, the display configured for providing a visual information related to the application of one or more consumer products. The device of this example may include a docking station/cradle for attaching the device. The device of this example may also include a motor for driving one or more motions of the applicator element. The one or more motions may include a motion selected from the group consisting of a rotary motion, an articulating motion, a pulsing motion, a wave motion, a sonic motion, and any combinations thereof. The device of this example may be portable.

Example components of a device for application of one or more consumer products to a surface of a user may be shown in the implementations, embodiments, and examples above as a single component. It is contemplated that a plurality of elements may replace a single component to provide the same or an improved functionality as the single component. It is also contemplated that a single component may be included in a device to provide the same or an improved functionality as a multiple of like components. Further, a component may be physically distributed (e.g., across an applicator device, one or more remote user devices, one or more base unit holders, or combinations thereof) to provide for same or an improved functionality as non-distributed components.

Various implementation example devices are illustrated above with exemplary components shown in each figure and described in the corresponding text. Other example devices can include any combination of the disclosed components and functionalities and remain true to the scope of the present invention. For example, components, elements, and functionalities disclosed in combination in a device (100, 200, 300, 400, 500, 600, 800, 900, 1500, 1600, 1700) may individually and/or in any sub-combination be combined with any component, element, and/or functionality of another device (100, 200, 300, 400, 500, 600, 800, 900, 1500, 1600, 1700) to form a different example device of the current disclosure.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:

1. A device for application of consumer products to an outer surface of a subject, the device including:
    a plurality of reservoirs, each of the plurality of reservoirs for holding a consumer product, at least two of the plurality of reservoirs are part of a cartridge removable from the device;
    an applicator element configured to apply one or more of the consumer products to an outer surface of a subject, wherein each of the at least two of the plurality of reservoirs is in contact with at least a portion of the applicator element, the applicator element being a part of the cartridge removable from the device;
    a pumping element connected to the plurality of reservoirs, the pumping element configured to deliver one or more of the consumer products to a first surface of the applicator element; and
    a processing element for controlling the pumping element to selectively deliver a first consumer product from a first one of the plurality of reservoirs to the applicator element in series and/or in combination with a second consumer product from a second one of the plurality of reservoirs.

2. A device according to claim 1, wherein the pumping element includes a piston component positioned in at least one of the plurality of reservoirs, the piston component actuated by a gas pressure to move the piston in a direction toward a consumer product within the at least one of the plurality of reservoirs.

3. A device according to claim 1, wherein the cartridge prior to initial connection with the device includes one or more physical barriers blocking one or more openings in the at least one of the plurality of reservoirs from exposure to air outside of the cartridge.

4. A device according to claim 1 further comprising a secondary applicator element, the secondary applicator element configured to contact the surface of the subject and, via motion, work the one or more consumer products into the surface of the subject.

5. A device according to claim 4, further comprising a motion driving mechanism connected to the secondary applicator element for providing the motion to the secondary applicator element.

6. A device according to claim 1, wherein the cartridge includes an identification element and the device further includes a reading element in communication with the processing element and configured to read one or more data from the identification element when the cartridge is connected to the device.

7. A device according to claim 2, further comprising a network connection and a memory element in operative communication with the processing element, the memory element including machine executable information for instructing the processing element to transfer data via the network connection element to a remote device, the data regarding an application of the one or more of the consumer products.

8. A device according to claim 7, wherein the data includes information selected from the group consisting of an identification of a consumer product within the cartridge, a sequence order for administering a plurality of consumer product, an expiration date of a consumer product within the cartridge, a prescription for a consumer fluid within the cartridge, an instruction for application of a consumer product within the cartridge, a dosing instruction for a consumer product within the cartridge, and any combinations thereof.

9. A device according to claim 2, further comprising a memory element in operative communication with the processing element, the memory element including machine executable information for instructing the processing element to operate the pumping element to provide a first portion of the first consumer product from the first one of the plurality of reservoirs, then a first portion of the second consumer product from the second one of the plurality of reservoirs, then a second portion of the first consumer product from the first one of the plurality of reservoirs, each portion provided in series to the applicator element.

10. A device for application of consumer products to an outer surface of a subject, the device including:
at least two reservoirs, each of the at least two reservoirs for holding a consumer product, the at least two reservoirs positioned in a removable cartridge, the removable cartridge including one or more connection elements for connecting the removable cartridge to the device;
an applicator element configured to apply one or more of the consumer products to an outer surface of a subject;
a pumping element connected to the at least two reservoirs, the pumping element configured to deliver one or more of the consumer products to a first surface of the applicator element, the pumping element including a piston component positioned in each of the at least two reservoirs, each piston component actuated by a gas pressure to move the piston in a direction toward a consumer product within the corresponding reservoir of the at least two reservoirs; and
a processing element for controlling the pumping element to selectively deliver a first consumer product from a first one of the at least two reservoirs to the applicator element in series and/or in combination with a second consumer product from a second one of the at least two reservoirs, wherein each of the first and second ones of the at least two reservoirs is in contact with at least a portion of the applicator element, the applicator element being a part of the cartridge removable from the device.

11. A device according to claim 10, further comprising a secondary applicator element, the secondary applicator element configured to contact the surface of the subject and, via motion, work the one or more consumer products into the surface of the subject.

12. A device according to claim 11, further comprising a motion driving mechanism connected to the secondary applicator element for providing the motion to the secondary applicator element.

13. A device according to claim 10, wherein the cartridge includes an identification element and the device further includes a reading element in communication with the processing element and configured to read one or more date from the identification element when the cartridge is connected to the device.

14. A device according to claim 10, further comprising a network connection and a memory element in operative communication with the processing element, the memory element including machine executable information for instructing the processing element to transfer data via the network connection element to a remote device, the data regarding an application of the one or more of the consumer products.

15. A device according to claim 14, wherein the data includes information selected from the group consisting of an identification of a consumer product within the cartridge, a sequence order for administering a plurality of consumer product, an expiration date of a consumer product within the cartridge, a prescription for a consumer fluid within the cartridge, an instruction for application of a consumer product within the cartridge, a dosing instruction for a consumer product within the cartridge, and any combinations thereof.

16. A method of applying a plurality of consumer products to a surface of a subject with an automated application device, the automated application device including an application element and a plurality of reservoirs, each of the plurality of reservoirs configured to contain a consumer product and provide the consumer product to the application element, the plurality of reservoirs positioned in a cartridge, the cartridge removably connectable to the automated application device, the method comprising:
automatically providing a first pressure on a first consumer product in a first reservoir of the plurality of reservoirs, the first pressure delivering a first portion of the first consumer product to a surface of an applicator element of the automated application device, the applicator element being a part of the cartridge;
contacting the applicator element with the first consumer product to the surface of the subject;
providing an automatic motion to the applicator element;
providing a second pressure on a second consumer product in a second reservoir of the plurality of reservoirs after the contacting the applicator element to the surface of the subject, the second pressure delivering a first portion of the second consumer product to a surface of the applicator element; and
contacting the applicator element with the second consumer product to the surface of the subject.

17. A method according to claim 16, further comprising:
providing a third pressure on the first consumer product in the first reservoir, the third pressure delivering a second portion of the first consumer product to a surface of the applicator element;
contacting the applicator element with the second portion of the first consumer product to the surface of the subject.

* * * * *